United States Patent
Dial

(10) Patent No.: US 10,359,408 B2
(45) Date of Patent: Jul. 23, 2019

(54) SYSTEM AND PROCESS FOR JET FUEL EQUIPMENT AND PROCEDURE QUALITY CONTROL

(71) Applicant: Wingware, LLC, Dallas, TX (US)

(72) Inventor: Kent Dial, Dallas, TX (US)

(*) Notice: Subject to any disclaimer, the term of this patent is extended or adjusted under 35 U.S.C. 154(b) by 408 days.

(21) Appl. No.: 14/964,572

(22) Filed: Dec. 9, 2015

(65) Prior Publication Data
US 2017/0176407 A1  Jun. 22, 2017

Related U.S. Application Data

(60) Provisional application No. 62/089,831, filed on Dec. 9, 2014.

(51) Int. Cl.
*G01N 33/22* (2006.01)
*G06Q 10/10* (2012.01)
*G06Q 50/30* (2012.01)

(52) U.S. Cl.
CPC .......... *G01N 33/225* (2013.01); *G06Q 10/10* (2013.01); *G06Q 50/30* (2013.01)

(58) Field of Classification Search
CPC .. G06Q 10/06; G06Q 10/06395; G06Q 50/06; G06Q 50/30; C10L 2270/04; G07C 5/008; G06F 3/04842; G01N 33/225
USPC .................... 340/539.24; 700/272; 701/34.4; 702/182, 183; 707/E17.032
See application file for complete search history.

(56) References Cited

U.S. PATENT DOCUMENTS

| | | | | |
|---|---|---|---|---|
| 8,165,848 B2* | 4/2012 | Knight | ................... | G06Q 10/20 702/182 |
| 8,239,252 B2* | 8/2012 | Wellman | ............... | G05D 1/0282 705/7.29 |
| 9,632,009 B2* | 4/2017 | Berger | ................... | G01M 15/14 |
| 2002/0156692 A1* | 10/2002 | Squeglia | ............. | G06Q 10/087 705/26.81 |
| 2004/0051862 A1* | 3/2004 | Alcock | ................ | G01N 21/474 356/71 |

(Continued)

OTHER PUBLICATIONS

Air Transport Association of America, Inc. (2006), "ATA Specification 103—Standard for Jet Fuel Quality Control at Airports," Revision 2006.1, 1301 Pennsylvania Ave., N.W., Suite 1100, Washington, D.C. 20004-1707.*

(Continued)

*Primary Examiner* — John E Breene
*Assistant Examiner* — Jeffrey P Aiello
(74) *Attorney, Agent, or Firm* — John Lindsay

(57) ABSTRACT

The present invention is directed to a system and process for monitoring jet fuel quality control procedural compliance. One system of the current invention includes a portable computer in communication with a server over network, an equipment database, and a report module. In exemplary process, jet fuel equipment is input into the system and stored in the equipment database, along with the process for its inspection. Inspector profiles are input into the system. The system facilitates notification of required inspections for a facility. The system presents an interface guiding an inspector through inspection of jet fuel and jet fuel equipment inspections. The input is stored by the system, whereby the report module generate reports based on inspection reports, equipment, and facilities.

6 Claims, 47 Drawing Sheets

(56) References Cited

U.S. PATENT DOCUMENTS

| | | | | |
|---|---|---|---|---|
| 2005/0171661 | A1* | 8/2005 | Abdel-Malek | B61L 27/0094 |
| | | | | 701/31.4 |
| 2006/0087402 | A1* | 4/2006 | Manning | G05B 19/41875 |
| | | | | 340/3.1 |
| 2006/0157143 | A1* | 7/2006 | Memmott | G05B 15/02 |
| | | | | 141/198 |
| 2007/0203660 | A1* | 8/2007 | North | G06Q 10/06 |
| | | | | 702/83 |
| 2008/0006089 | A1* | 1/2008 | Adnan | F04B 51/00 |
| | | | | 73/587 |
| 2009/0064755 | A1* | 3/2009 | Fleischli | A61M 1/3663 |
| | | | | 73/1.16 |
| 2009/0157521 | A1* | 6/2009 | Moren | G06Q 10/10 |
| | | | | 705/1.1 |
| 2010/0171624 | A1* | 7/2010 | McSheffrey | G08B 25/10 |
| | | | | 340/614 |
| 2014/0039648 | A1* | 2/2014 | Boult | G05B 15/02 |
| | | | | 700/79 |
| 2015/0009013 | A1* | 1/2015 | Cartwright | G06Q 10/087 |
| | | | | 340/10.1 |
| 2015/0195763 | A1* | 7/2015 | Chen | H04W 36/18 |
| | | | | 455/436 |

OTHER PUBLICATIONS

Air Transport Association of America, Inc. (2006), "ATA Specification 103—Standard for Jet Fuel Quality Control at Airports," Revision 2006.1, 1301 Pennsylvania Ave., N.W., Suite 1100, Washington, D.C. 20004-1707. (Year: 2006).*

* cited by examiner

Fig. 3e

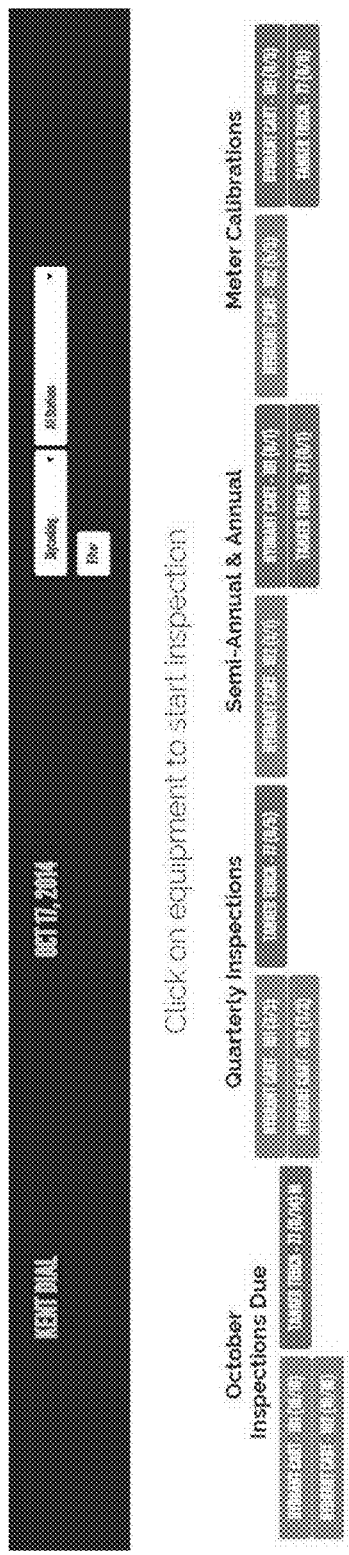

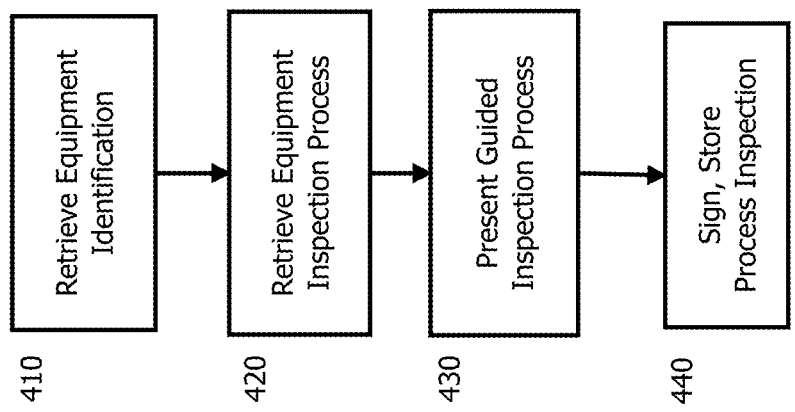

Steps:

Vessel Nameplate secure and legible. Conversion date plate installed, if applicable.

| Satisfactory | Comment | Not Applicable |

Verify that Similarity Date Sheets are on file & have been updated to reflect API 1581 Latest Edition if applicable.

| Satisfactory | Comment | Not Applicable |

Base mounting bolts secure.

| Satisfactory | Comment | Not Applicable |

Steps:

Shutdown and lockout pump | Satisfactory | Comment | Not Applicable

Close Inlet/Outlet valves and open vent | Satisfactory | Comment | Not Applicable Drain Fuel | Satisfactory | Comment | Not Applicable

Fig. 7d

Steps:
- Close drain valve(s) — Satisfactory | Comment | Not Applicable
- Ensure Air Eliminator is open — Satisfactory | Comment | Not Applicable
- Remove Lock and Start Pump — Satisfactory | Comment | Not Applicable
- Slightly open inlet valve to slowly fill vessel

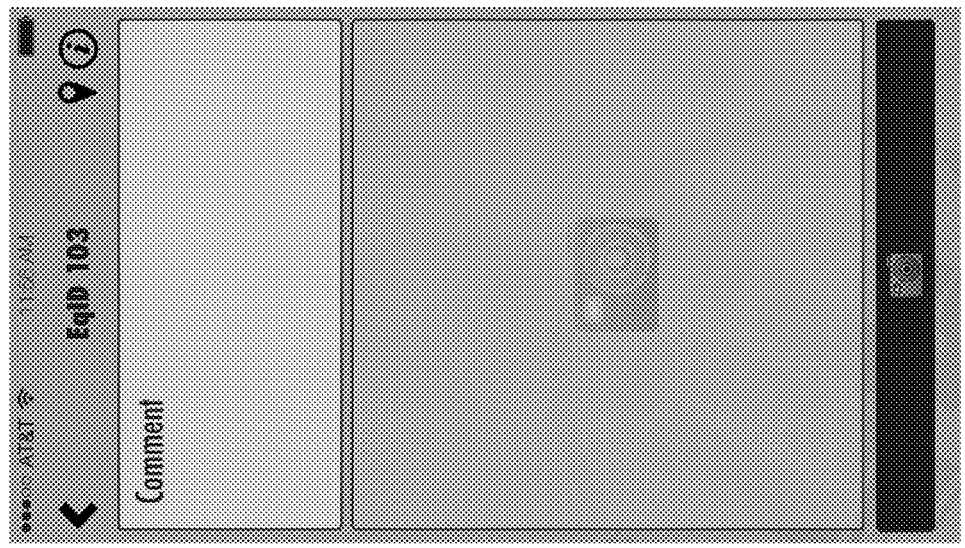

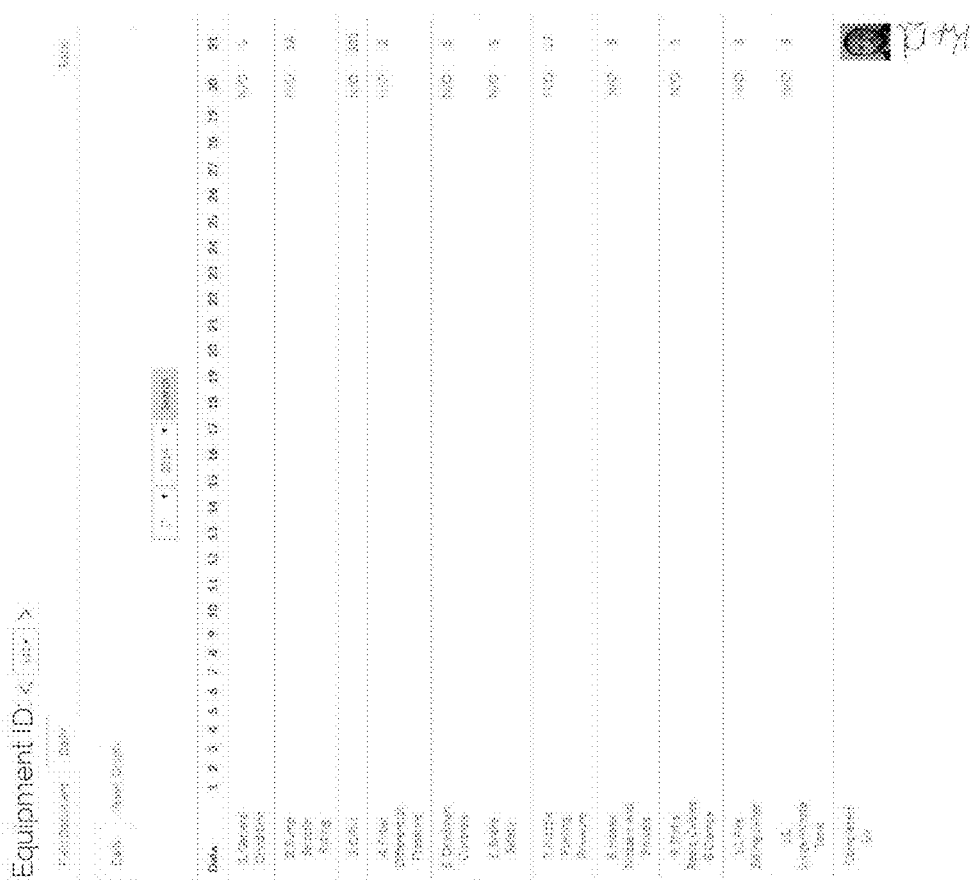

Equipment ID: < 102 ▾ >

Field Document | Daily

[ 03/10/2014 ] [ Search ]

| Step | Value | Points | Performed by | Time |
|---|---|---|---|---|
| General Condition | 0 | 2.25 | Kent Olis | 19:43:35 |
| Sump Sample Rating | 1A | 6.00 | Kent Olis | 19:44:37 |
| GPM | 0.00 | 0.00 | Kent Olis | 19:44:44 |
| Filter Differential Pressure | 2 | 8.50 | Kent Olis | 19:44:52 |
| Deadman Controls | 0 | 9.75 | Kent Olis | 19:45:01 |
| Brake Safety Interlocks | 0 | 4.50 | Kent Olis | 19:45:26 |
| Nozzle Fueling Pressure | 35 | 7.50 | Kent Olis | 19:45:35 |
| Hoses, Nozzles, and Swivels | 0 | 9.00 | Kent Olis | 19:45:37 |
| Static Reels, Clicks & Clamps | 0 | 2.50 | Kent Olis | 19:45:38 |
| Fine Strainer(s) | 0 | 2.50 | Kent Olis | 19:45:40 |
| Surge/Waste Tank | 0 | 4.00 | Kent Olis | 19:47:00 |

Fig. 9

Flash Audit Item List

Back To Home

Pending Items

- Fire Extinguishers > Inact seal
  Hydrant Cart - 101
  0:57:02  Start

- Fire Extinguishers > Inact seal
  Hydrant Cart - 105
  0:57:02  Start

- Fire Extinguishers > Inact seal
  Hydrant Cart - 109
  0:57:02  Start

- Fire Extinguishers > Inact seal
  Hydrant Cart - 113
  0:57:02  Start

Fig. 161

Fire Extinguishers > Inact seal

Hydrant Cart - 101

*0:55:59*

Comment

*Select Choose File to take a photo or upload one from your library.

Upload Photo    [Choose File] No file chosen

[Complete]    [Cancel]

Fig. 10j

Fire Extinguishers > Inact seal

Hydrant Cart - 101

0:52:14

Comment

[Intact Seal Test Photo]

*Select Choose File to take a photo or upload one from your library.

Upload Photo   Choose File  IMG_0254.jpg

Complete        Cancel

Fig. 10k

SYSTEM AND PROCESS FOR JET FUEL EQUIPMENT AND PROCEDURE QUALITY CONTROL

PRIORITY

The present invention claims priority to provisional application 62/089,831, which has a filing date of Dec. 9, 2014.

BACKGROUND

Field of the Invention

The present invention relates to systems and processes for jet fuel equipment safety, specifically for systems and processes for jet fuel equipment and procedure quality control.

Description of the Related Art

Those in the industry recognize the importance of using quality jet fuel for ensuring the highest degree of flight safety. To achieve this goal, airports employ jet fuel quality control standards which cover fuel distribution facilities and fuel quality control procedures.

The standards identify industry inspection procedures and safety checks of jet fuel storage and distribution facilities at airports that will help minimize problems such as introduction of contaminated or unacceptable jet fuel from being delivered to airline aircraft. Individual airports or other facilities may employ custom testing procedures based on fuel system complexity and local operating conditions. The baseline procedures, as well as alternative procedures, and use of non-standard facilities and equipment may also be recognized and determined acceptable for achieving the above safety requirements based on all circumstances.

For safety and auditing, the equipment, people, and facility's conformance to the standards should be documented. Currently, the process provides inadequate integrity and authentication. It would be advantageous to have a system and process for jet fuel quality procedure monitoring which readily facilitates higher integrity monitoring of the equipment and increased performance of the people and facility.

SUMMARY

The present invention is directed to a system and process for monitoring jet fuel quality control procedural compliance. One system of the current invention includes a portable computer in communication with a server over network, an equipment database, and a report module. In exemplary process, jet fuel equipment is input into the system and stored in the equipment database, along with the process for its inspection. Inspector profiles are input into the system. The system facilitates notification of required inspections for a facility. The system presents an interface guiding an inspector through inspection of jet fuel and jet fuel equipment inspections. The input is stored by the system, whereby the report module generate reports based on inspection reports, equipment, and facilities.

These and other features, aspects, and advantages of the invention will become better understood with reference to the following description, and accompanying drawings.

BRIEF DESCRIPTION OF THE DRAWINGS

FIGS. 3a-3f depict representative screens for input of jet fuel equipment;

FIGS. 5a-5h depict representative screens for inspection notification;

FIG. 6 depicts a flow chart of major steps of an embodiment of a jet fuel quality control compliance inspection subprocess of the current invention;

FIGS. 7a-7g depict representative screens for the inspection process;

FIGS. 8a-8c depict representative output of the report module;

FIG. 9 shows a report of completed inspections with assigned values; and

DETAILED DESCRIPTION

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

The present invention is directed to for systems and processes for jet fuel equipment and procedure quality control. Embodiments of the invention include systems and processes for monitoring compliance of airport jet fuel storage facilities, hydrant distribution systems, and aircraft refueling equipment in order to effectively ensure the safe and dependable flow of quality jet fuel to airline aircraft.

Figure 1:
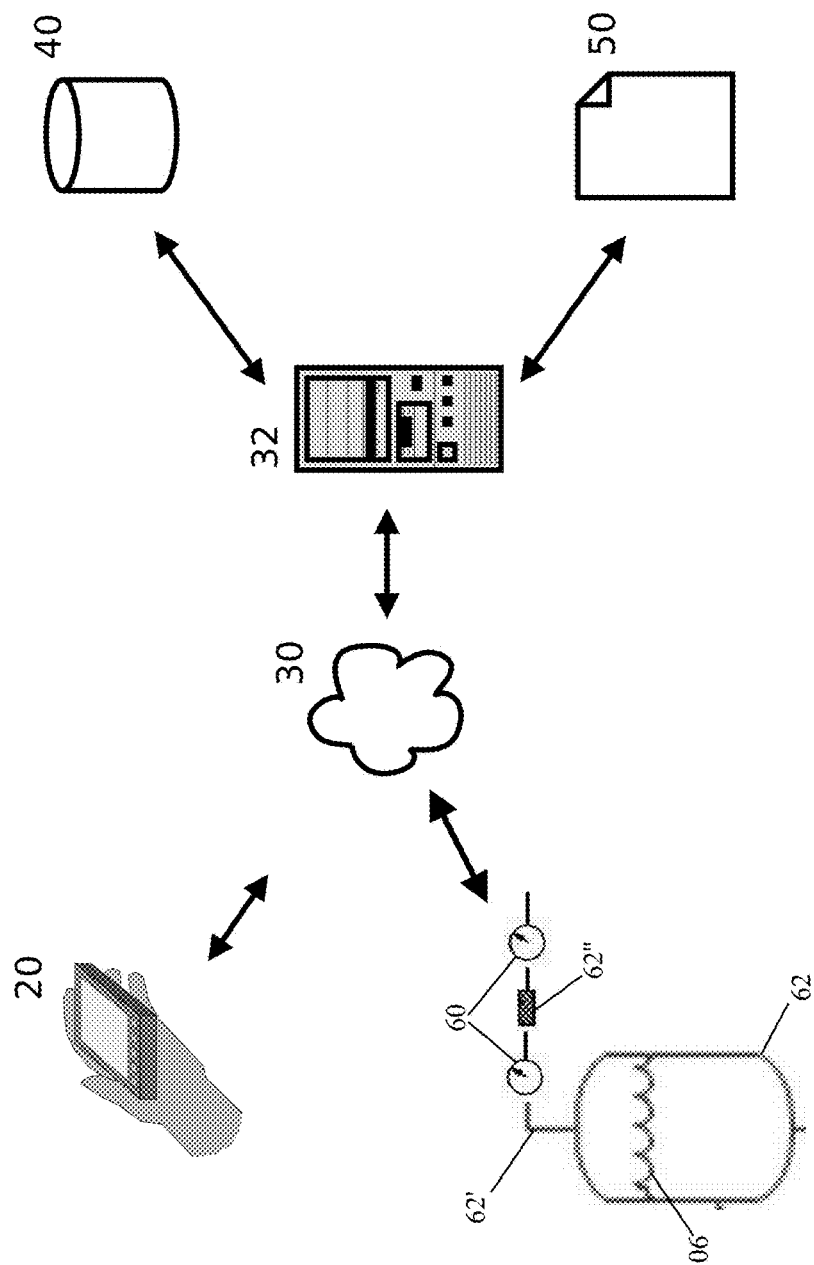
FIG. 1 depicts a block diagram of major components of an embodiment of a jet fuel quality control compliance system of the current invention.

FIG. 1 illustrates an embodiment of a system according to the present invention as it may exist in operation. Depicted are a portable computer 20 having an inspection module 70, a communication network 30, a server 32 having an equipment module 80, representative jet fuel equipment 62 (storage tank 62, fuel line 62', fuel filter 62"), sensors 60 deployed to the jet fuel equipment, an equipment database 40, and a report module 50. In exemplary use, the jet fuel equipment 62 of a facility is input into the system 100, inspector profiles are input into the system 200, jet fuel equipment inspections are input into the system 300, the jet fuel equipment is monitored 400, and periodic inspection reports are processed and analyzed.

A computer, as referred to in this specification, generally refers to a system which includes a processor, memory, a screen, a network interface, and input/output (I/O) components connected by way of a data bus. The I/O components may include for example, a mouse, keyboard, buttons, or a touchscreen. The network interface enables data communications over the network 30. An exemplary server 32 is a computer contains various server software programs and application server software. An exemplary portable computer 20 is a handheld computer, smartphone, or tablet computer, wearable (eg glasses, watches), such as an iPhone, iPod Touch, iPad, Blackberry, Android based device, or other similar computer. The portable computer 20 is optionally configured with a touch screen and integrated camera elements. An exemplary camera is a color digital camera integrated with the portable computer 20. Those skilled in the art will appreciate that the computer 20 or servers 32 can take a variety of configurations, including personal computers, hand-held devices, multi-processor systems, microprocessor-based electronics, network PCs, minicomputers, mainframe computers, and the like. Additionally, the portable computer 20 or servers 32 may be part of a distributed computer environment where tasks are performed by local and remote processing devices that are communicatively linked. Although shown as separate devices, one skilled in the art can understand that the structure of and functionality associated with the aforementioned elements can be optionally partially or completely incorporated within one or the other, such as within one or more processors.

The illustrated system provides an equipment module 80 with instructions to be carried out by the server 32 and an inspection module 70 to be carried out on the portable computer 20.

The communication network 30 includes a computer network and/or a telephone system. The communication network 30 includes of a variety of network components and protocols known in the art which enable computers to communicate. The computer network 30 may be a local area network or wide area network such as the internet. The network 30 may include modem lines, high speed dedicated lines, packet switches, etc. The network protocols used may include those known in the art such as UDP, TCP, IP, IPX, or the like. Additional communication protocols may be used to facilitate communication over the computer network 30, such as the published HTTP or HTTPS protocol used on the world wide web or other application protocols.

The system includes specialized storage in the form of an equipment database 40 configured to store jet fuel equipment data, inspector data, inspection data, report data and other data. Exemplary databases include a table having rows, "slices," or other data structures created to store the data. One skilled in the art would appreciated that the data may reside in one or more databases, tables, or computers. Representative suitable database systems include MySQL, PostgreSQL, SQLite, Microsoft SQL Server, Oracle, or dBASE.

Jet fuel equipment 62 includes equipment used in the receipt, storage, and distribution of jet fuel and related activity, such as safety issues involved in jet fuel handling activity. Representative jet fuel equipment 62 for inspection and monitoring include jet fuel and jet fuel equipment. Representative jet fuel equipment includes, but is not limited to jet fuel, storage tanks, fuel lines, fuel filters, transport trucks, refuelers, hoses, fuel valves, isolation valves, pumps, pressure equalizers, hydrant carts, hydrant systems, separators, fuel shutoffs, fire extinguishers, signage, relaxation chambers, bulk air eliminators, refueling truck loading station, drains, vents, surge absorbers, leak detection and piping isolation systems, filter/separator or full flow fuel monitor, pressure controls, deadman control systems, dust covers, strainers, swivels, aircraft fuel pressure gauges, fuel quantity measurement meter, electrostatic bonding system, and other jet fuel equipment known in the art.

Embodiments of the current invention are configured to receive input from sensors 60 directly or through human input. Sensor 60, as used within the specification mean a device that measures a physical property within the subject environment and converts it into a signal which can be read by an observer or device. In the exemplary output for this invention, the sensor 60 output is transformed to an electrical signal encoding the measured property. It is to be understood that sensors may output in other formats such as alphanumeric, visual indicators, or other formats known in the art. The sensor 60 may incorporate a power source and local memory for storage of output, time stamps, and related data. Representative suitable sensors include, but are not limited to pressure sensors, light sensors, chemical sensors, temperatures sensors, voltage sensors. For example, a pressure sensor 60 provides a basis for fuel pressure and a light sensor provides a basis for fuel clarity.

Figure 2:
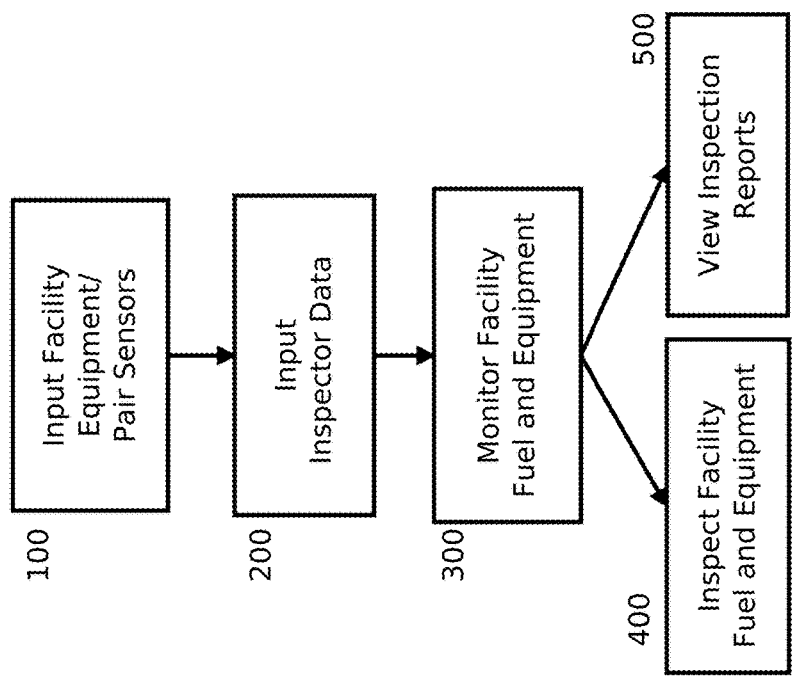
FIG. 2 depicts a flow chart of major steps of an embodiment of a jet fuel quality control compliance process of the current invention.

FIG. 2 depicts an embodiment of a process according to the current invention. The process includes inputting facility jet fuel equipment 100, inputting inspector data 200, monitoring facility jet fuel and jet fuel equipment 300, inspecting facility jet fuel and jet fuel equipment 400, and viewing inspection reports and compliance 500. More consideration will be given to each of these steps below.

Figure 3A:
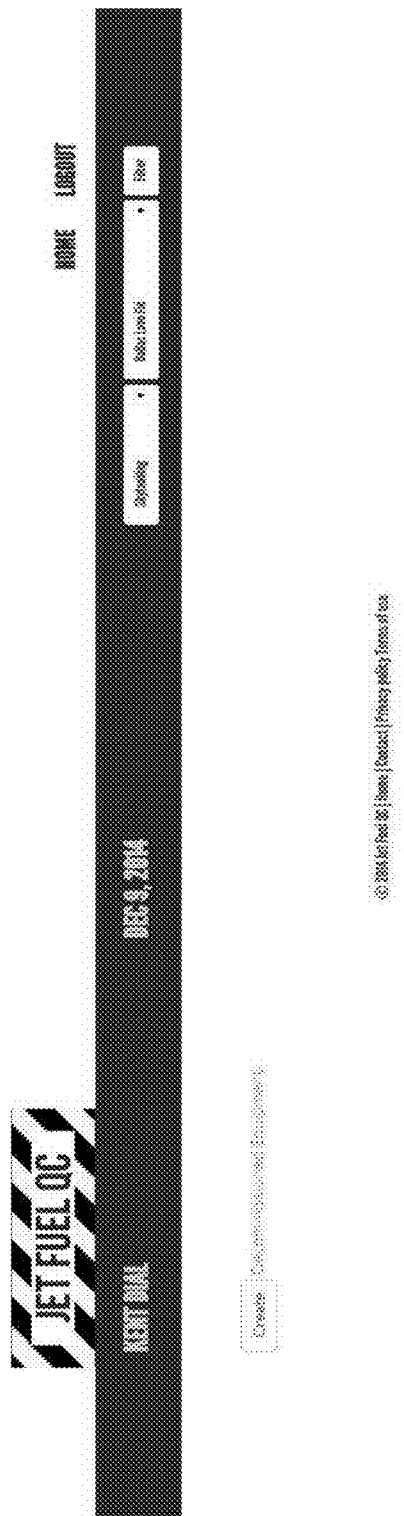
Figure 3B:
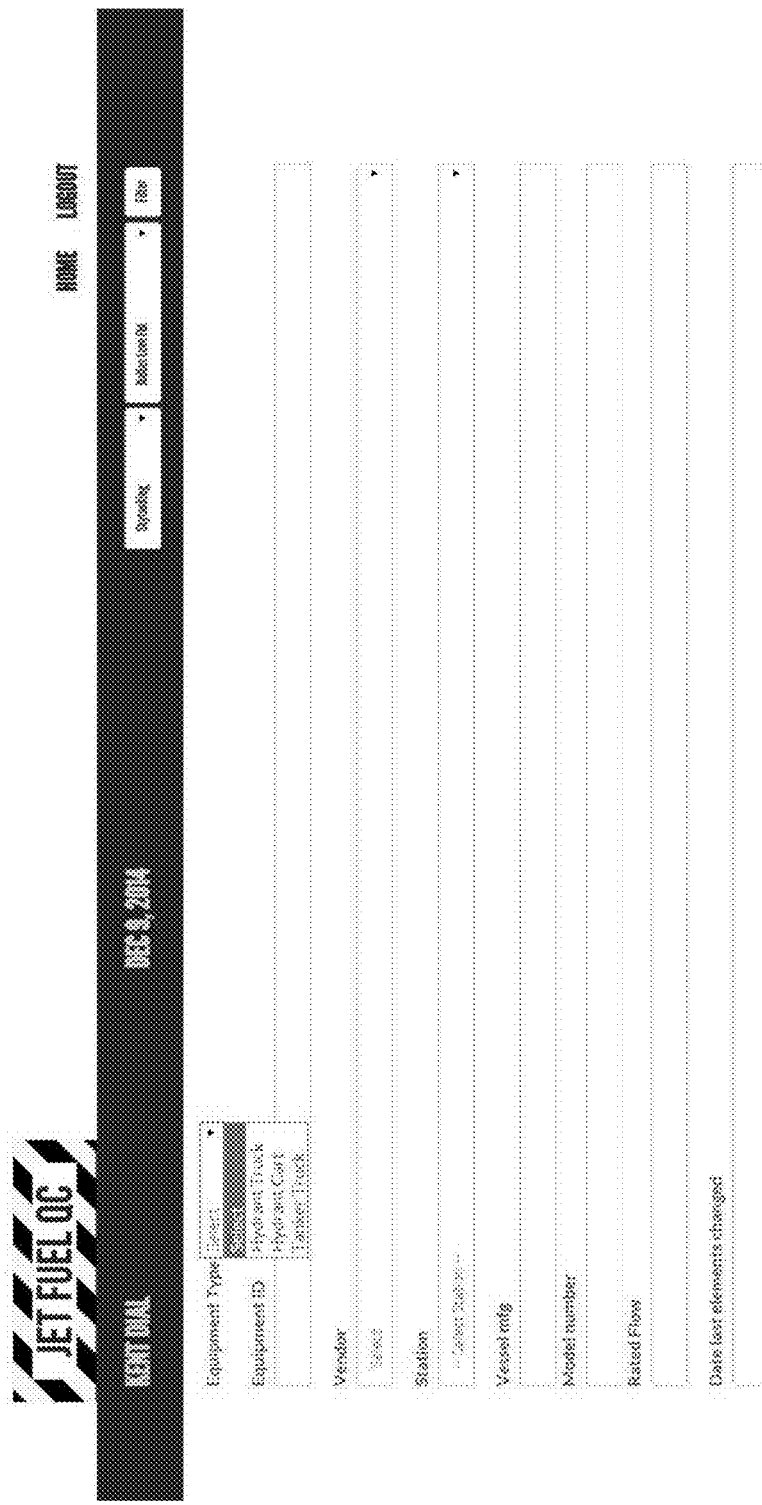
Figure 3C:
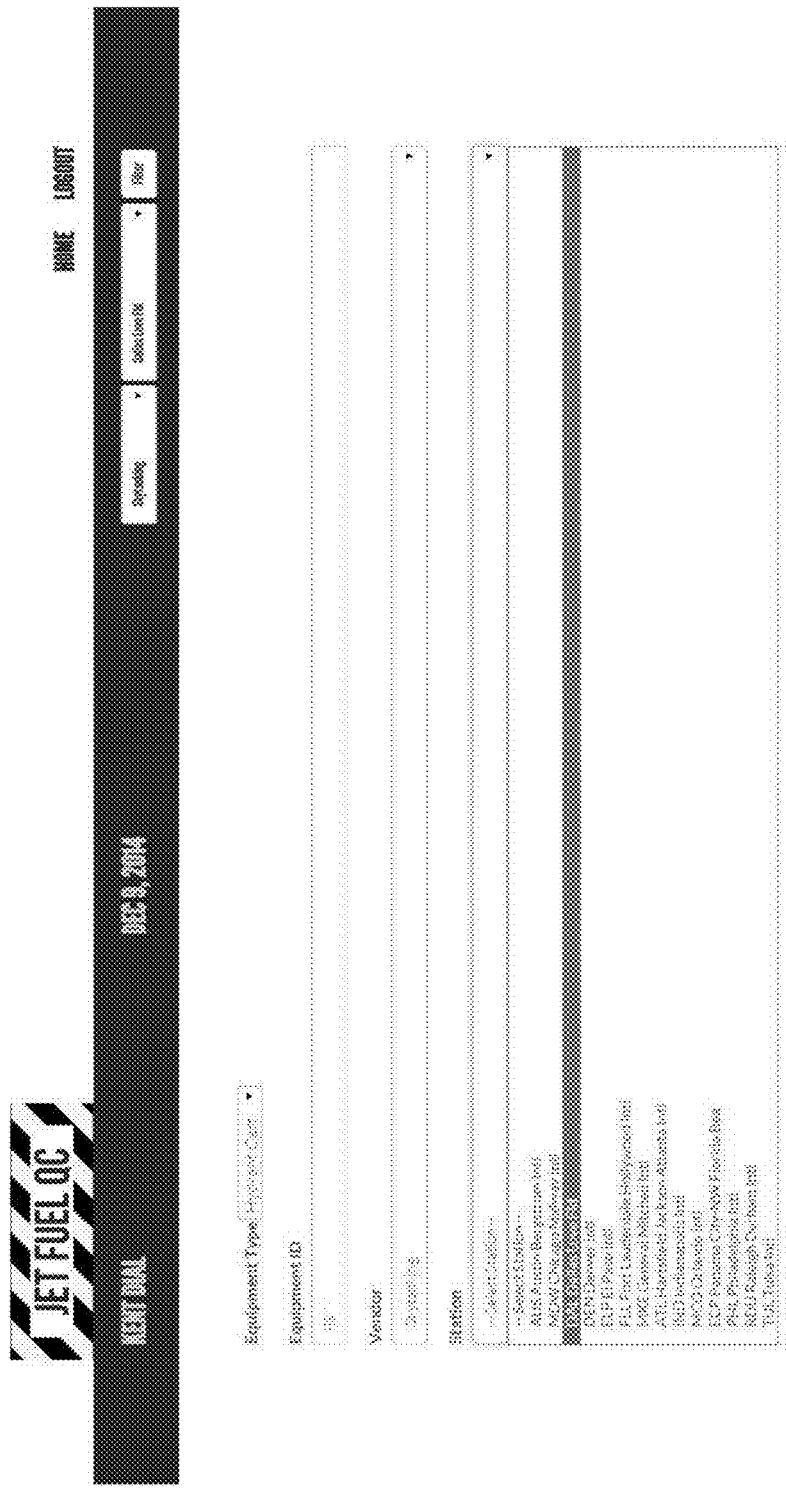
Figure 3D:
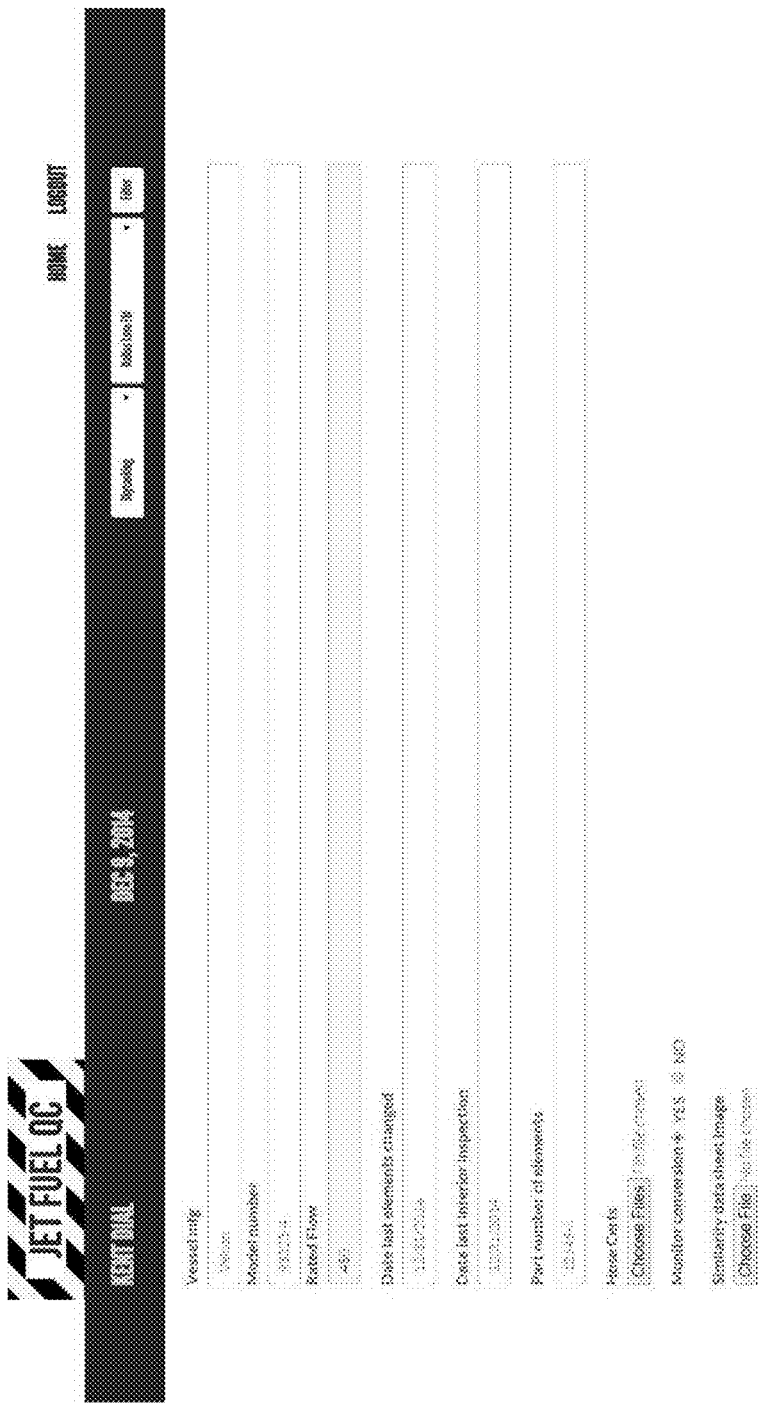
Figure 3E:
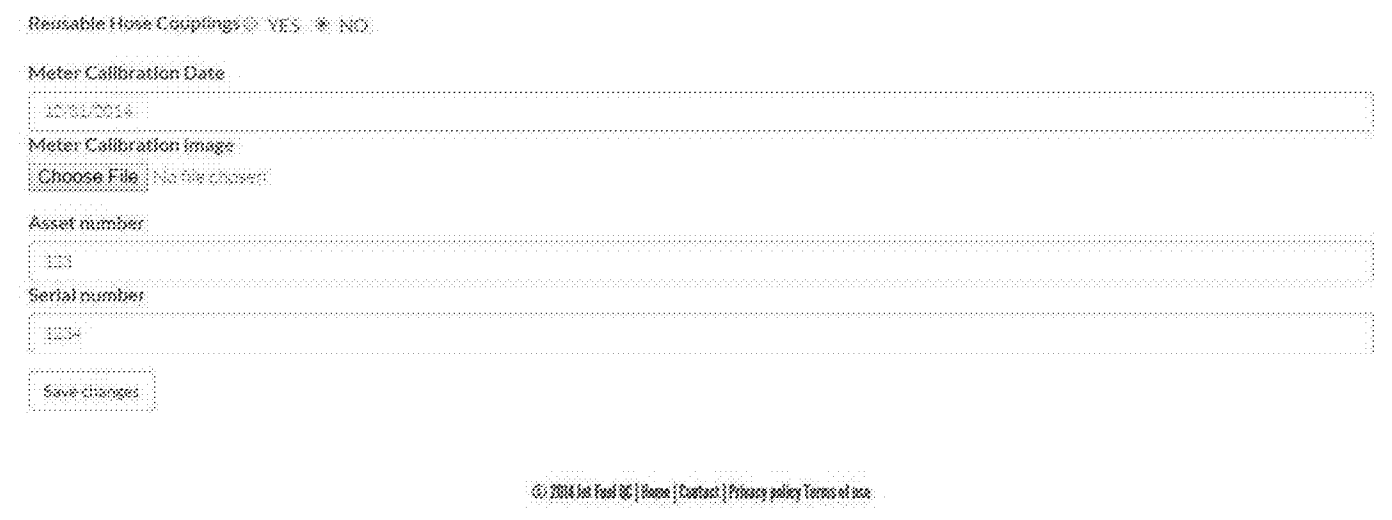
Figure 3F:
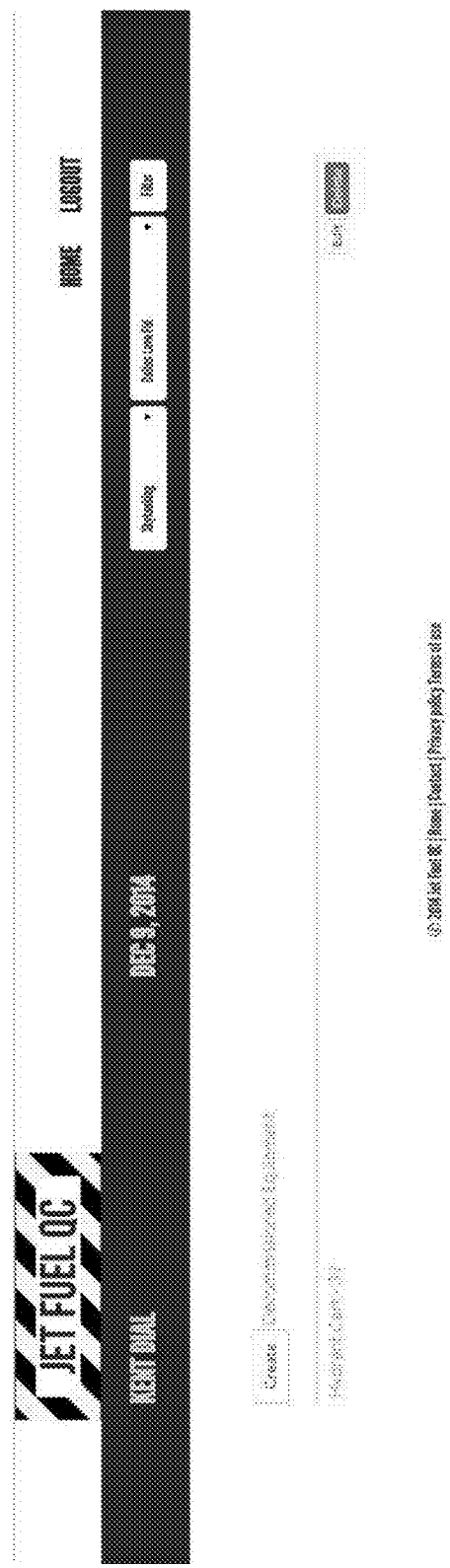

At step 100, the jet fuel equipment 62 is input into the system. When new, additional, replacement, or modified airport fuel storage, distribution facilities or aircraft refueling equipment is placed into operation, it is input into the system. In exemplary operation, an equipment type, equipment identifier, facility location, and time zone are input and stored in the equipment database 40 for each piece of equipment. In further exemplary process, an inspection process and inspection frequency is associated with the equipment, which will be disclosed further below. Optionally, a user name, user identifier, group name, group identifier, or user type is associated with the equipment in order to facilitate assigning an inspection. FIGS. 3*a*-3*f* depict a series of interfaces presented of the equipment module 80 to a user in one configuration. The equipment module 80 presents an interface for the user to input equipment (FIG. 3*a*). The equipment module 80 interface presents an input for the jet fuel equipment 62 type and equipment identifier (FIG. 3*b*). The equipment module 80 interface presents an input for station where the jet fuel equipment 62 type is located (FIG. 3*c*). The equipment module 80 interface further presents inputs for model number, calibration information, performance values, and other information for the jet fuel equipment 62 type is input (FIGS. 3*e* and 3*e*). The equipment module 80 stores the input in the equipment database 40.

In certain configurations, sensors 60 are associated with the jet fuel equipment 62. In exemplary configuration, the equipment module 80 interface presents inputs for the associated sensor 60, sensor type, and a sensor identifier. The input of the sensor information associated with the jet fuel equipment is stored in the input in the equipment database 40.

In exemplary configuration, one or more inspection processes is associated with the input jet fuel equipment 62, the inspection processes corresponding to the type of input jet fuel equipment 62. Representative inspections include, but are not limited to jet fuel upstream of airport receiving filtration, jet fuel purity downstream of the receiving and dispensing filtration as received into airport storage tanks and dispensed from airport storage facilities which will issue product directly, jet fuel purity downstream of the receiving and dispensing filtration as dispensed into aircraft.

Other representative inspections include jet fuel being brought into airport storage. These inspection requirements can vary depending on the method of delivery and facility layout. Receipts of jet fuel at airports are normally made by dedicated or multi-product pipelines, and highway transport trucks. There are some facilities receiving product directly from railroad tank cars or marine vessels. The facility operator recognizes that each of these transportation methods has different inspection requirements and that they may be addressed in local receiving procedures to ensure fuel quality and safety.

Other representative inspections include fuel storage facilities. Fuel storage facilities which supply fuel directly into aircraft, refuelers, or hydrant systems. Inspected items include storage tanks, filter/separators, emergency fuel shut-off system, fire extinguishers with inspection tags, fuel loading and unloading hoses, signage ("No Smoking," "Flammable") and product identification signs display, fuel storage facilities identification and color coding, metal underground tanks and piping cathode protection, relaxation chambers, bulk air eliminators, refueling truck loading station, product reclamation storage tank, fuel storage facilities.

Other representative inspections include tank yard inspection. Inspections include the general condition of tank yard (for example, appearance and cleanliness, plugged drainage, weeds, poor housekeeping, evidence of recent fuel spills, strong fuel odors, or the presence of fuel in catchment basins, overflow tanks, oil/water separators, or sumps).

Other representative inspections include security, fire, and safety deficiencies. Inspections include security, fire and safety deficiencies of fuel leaks, tanks, piping, valves, hoses, meters, filters, and other fuel handling equipment for fuel leaks.

Other representative inspections include storage tank and product reclamation tank sumps, filter sumps, filter differential pressure, hoses, swivels, nozzles and couplers, static reels, cables and clamps, filtration and free water testing, bonding cable continuity, nozzle screens, floating suctions, water defense systems, tank high level controls, product reclamation tank interior inspection, hose pressure checks, storage tank interiors, filter differential pressure gauges, filter elements, filter/separator heaters, tank vents, cathodic protection, line strainers, water defense system, hydrant system, hydrant pit, isolation valve pits and control vaults.

Other representative inspections include hydrant carts, hydrant valve assembly, low point drains, high point vents, surge absorbers, leak detection and piping isolation systems, filter/separator or full flow fuel monitor, pressure controls, deadman control systems, aircraft fueling hoses, manual isolation valves, dust covers, strainers and swivels, aircraft fuel pressure gauges, fuel quantity measurement meter, electrostatic bonding system, and refueling trucks. Representative inspections are include in the annexed ATA 103 specification, which is hereby incorporated by reference.

Figure 4A:
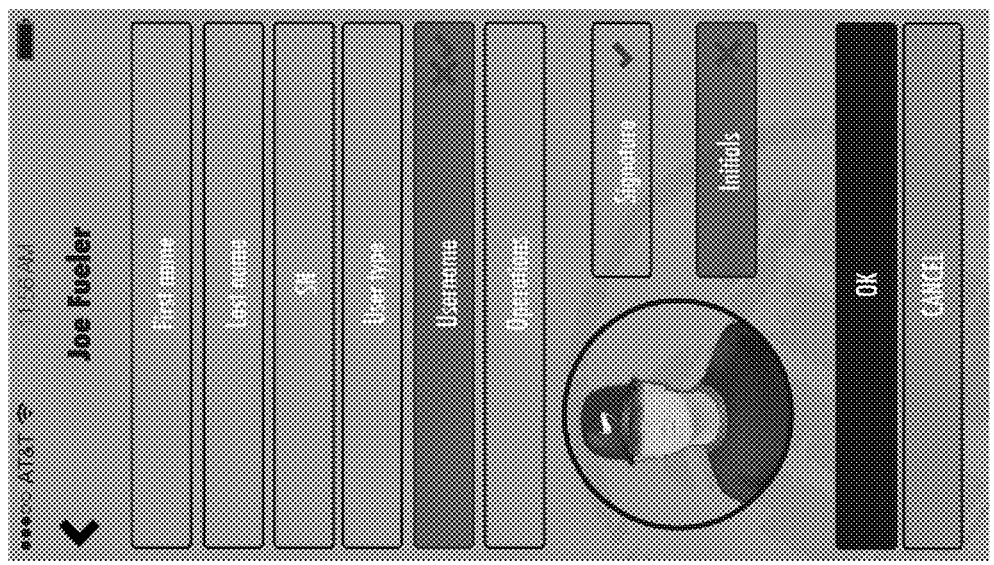
FIGS. 4a-4d depict representative screens for input of inspector profiles.
Figure 4B:
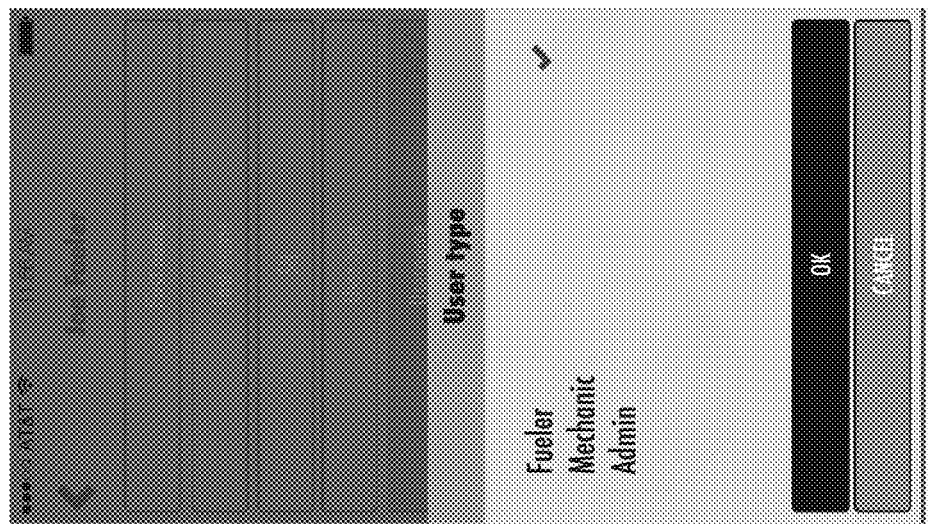
Figure 4C:
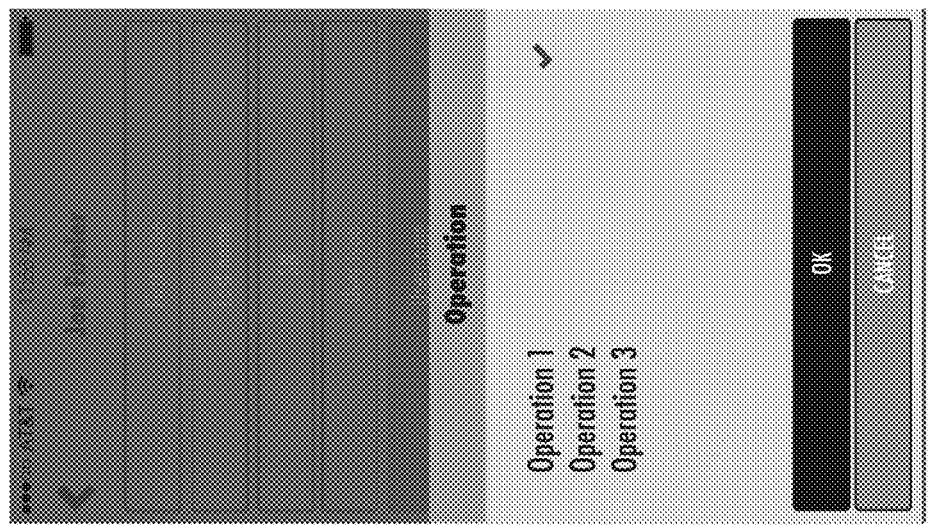
Figure 4D:
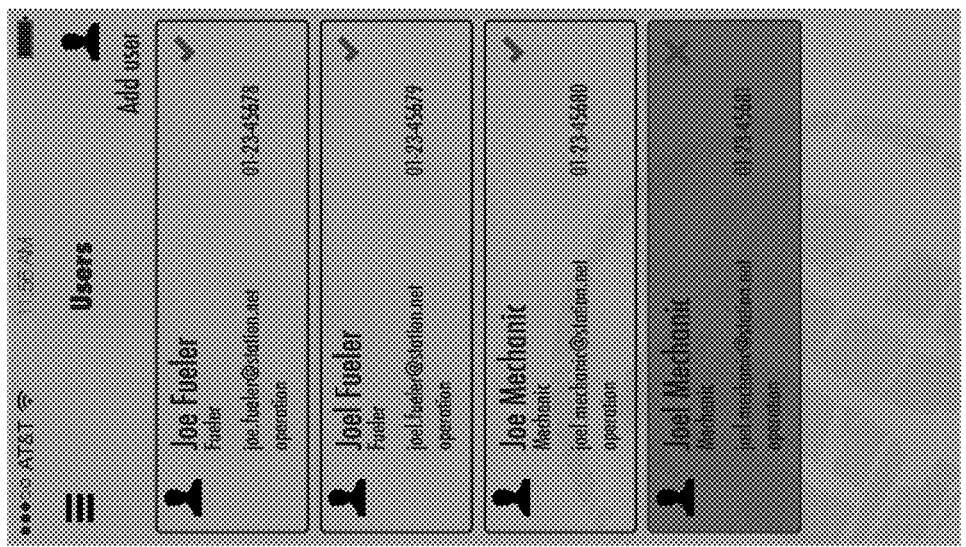

At step 200, inspector profiles are input into the system for storage in the equipment database 40. In exemplary operation, a user name, user identifier, user type (such as a group name or group identifier), contact information, credentials, and facility location are input and stored in the database 40 for each inspector. FIGS. 4a-4d show representative interfaces at various stages of inspector profile input. FIG. 4a illustrates a representative profile input interface in an initial state. The equipment module 80 presents the user with inputs including a name, username, and group inputs. The user can input a photo. FIG. 4b illustrates the profile input interface where the user type can be input. FIG. 4c illustrates the profile input interface where the facility can be input. FIG. 4d illustrates a representative profile input interface after the inspector profile is input and stored in the equipment database 40.

Figure 5A:
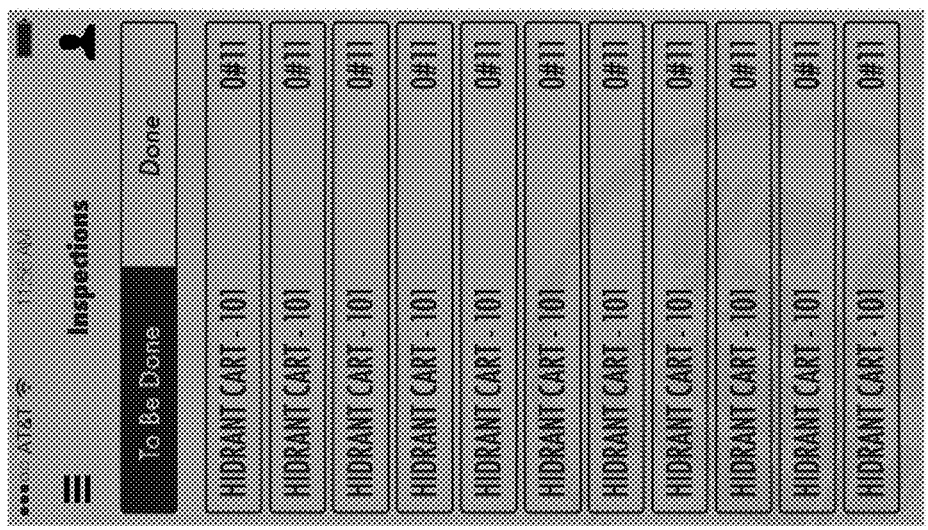
Figure 5B:
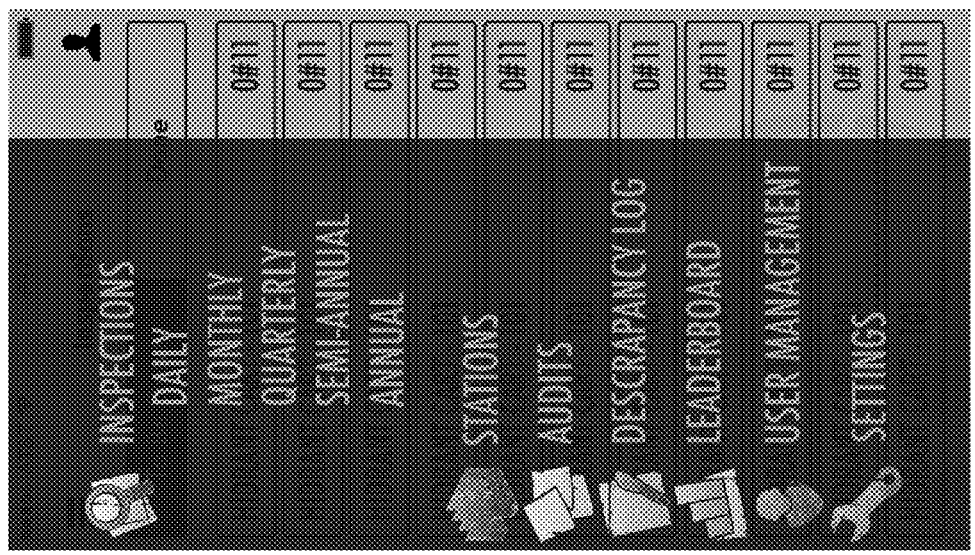
Figure 5C:
Figure 5D:
Figure 5E:
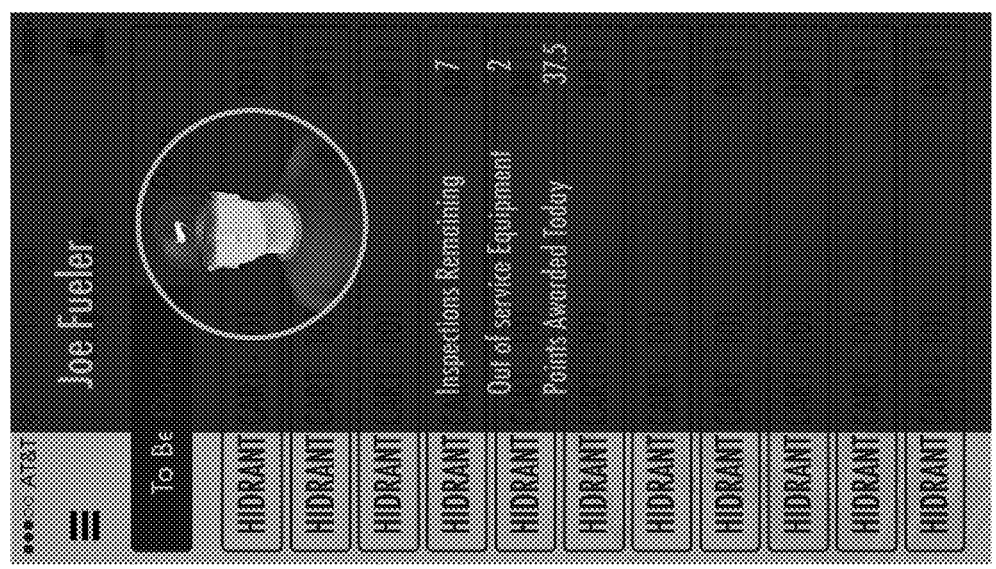
Figure 5F:
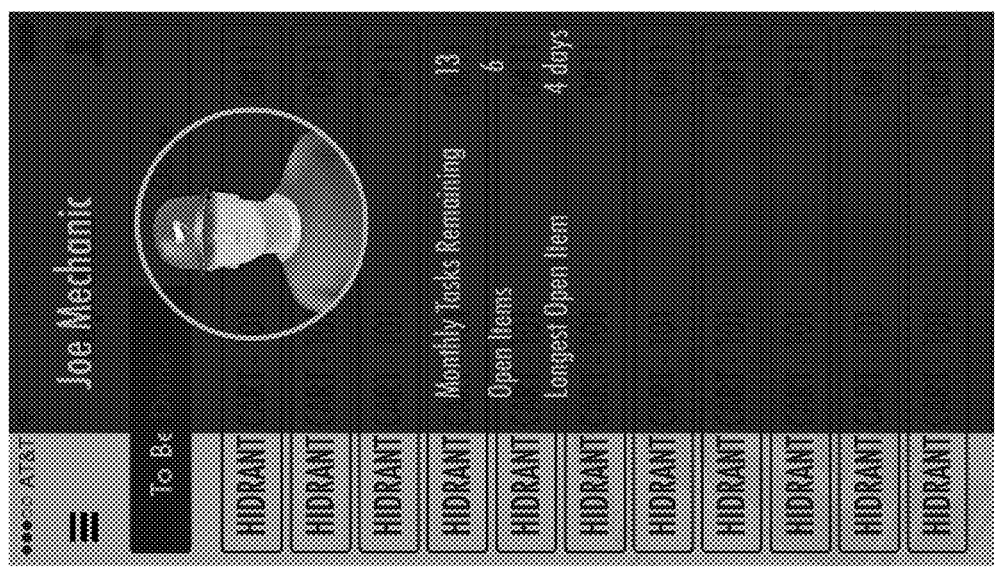

At step 300, the jet fuel and jet fuel equipment is monitored for the need to inspect and operating status. The need for inspection can be on a daily, monthly, quarterly, annual, other periodic basis, or triggered by event. The need for inspection can be initiated manually, system facilitated notifications, or by system notifications. In exemplary process, the equipment module 80 periodically scans the equipment database 40, retrieves the inspection frequency, retrieves the last inspection, and compares with the current date to determine the need for inspection. On an inspection condition, the equipment module 80 initiates a call to the inspection module 70 to initiate the inspection. In manual operation, the inspector initiates the need for inspection of jet fuel or jet fuel equipment and activates the inspection module 70. FIGS. 5a-5h show representative interfaces for system facilitated notice of need for inspection and inspection input into the inspection module 70. The inspection module 70 displays a list of pending inspections (FIG. 5a). An inspector logs in to the system. In one configuration, the inspection module 70 initially retrieves the inspector's user name, user type, and/or group membership. The inspection module 70 in communication with the equipment module 80 scans the equipment, retrieves the inspection frequency, retrieves the last inspection, and compares with the current date to determine the need for inspection by that user. A view is presented to the inspector showing the equipment requiring inspection. The inspector is prompted to initiate inspection. As an inspector completes inspections, progress is shown (FIGS. 5b-5g).

In certain embodiments of the system, inspections are triggered by analysis of sensor 60 data. As previously disclosed, sensors 60 can be paired with certain jet fuel equipment 62. The equipment module 80 processes one or more of real-time, near real-time and/or historical sensor data associated with the subject jet fuel equipment 62. Additionally, sensor 60 data processing of plural sensors 60 associated with the subject jet fuel equipment 62 may be employed, such as comparison. In certain configurations, an inspection is triggered when sensor 60 values are outside a predetermined range, above or below a threshold value. In certain configurations, historical sensor 60 data is processed to form trends, such as static values over time, increasing values over time, decreasing values over time, or erratic values over time. An inspection may be triggered where the trend is out of condition for the subject jet fuel equipment 62.

For example, for fueling equipment an inspection can be triggered when pressure sensor 60 output is above a threshold value. For instance, where fuel pressure values are greater than 40 psi, an inspection condition may be generated. For example, for fueling equipment an inspection can be triggered when pressure sensor 60 output is above a predetermined range. For instance, where fuel pressure values are greater than 41-45 psi, an inspection condition may be generated. For example, for fueling equipment an inspection can be triggered when pressure sensor 60 output is above a predetermined range. For instance, where fuel pressure values are greater than 41-45 psi, an inspection condition may be generated. For example, in plural sensor scenarios for fueling equipment, an inspection can be triggered by comparison of sensors 60 disposed at different points on the jet fuel equipment 62 and compared for a differential. For instance, where a fuel filter 62" is the subject jet fuel equipment 62, sensors 60 may be mounted upstream and downstream from the fuel filter 62". A zero pressure differential or significant pressure differential can trigger an inspection condition. For example, in equipment module 80 trend analysis for fueling equipment, an inspection can be triggered by comparison of sensor 60 data values over time. For instance, where a subject jet fuel equipment 62 has been used once a day for three days by three different inspectors and the value is the same, an inspection condition may be triggered. For instance, where a subject jet fuel equipment 62 has been used once a day for three days by one or more inspectors and the value is the same, an inspection condition may be triggered. A minimal difference in values or change toward a threshold can trigger an inspection condition.

At step 400, the jet fuel and jet fuel equipment is inspected. FIG. 6 illustrates a representative sub-process. As the jet fuel and jet fuel equipment are monitored 300, the need for an inspection arises and the subject item is queued for inspection. The inspection module 70 retrieves the equipment identifier, the equipment type, and assigned inspector(s) 410.

As previously disclosed, the system stores the inspection process for jet fuel or jet fuel equipment 62, each inspection process customized to each type of equipment in the equipment database 40. That is to say that the inspection process is different for each of the types of equipment listed above. Annexed ATA 103 provides additional information for inspections. The inspection module 70 retrieves the interface for the process for inspection of the subject equipment from library in the equipment database 420. The exemplary interface provides the inspection process and standard for inspection for the subject item.

For example, one of the inspection steps of jet fuel is to inspect the jet fuel for appearance and density. A standard for appearance of the jet fuel inspection is that the appearance of jet fuel should be clear and bright, visually free of undissolved water, sediment and suspended matter. The odor of the fuel should not be nauseating or irritating. The color of jet fuel should generally ranges from water white to light straw or amber. Other colors may be an indication the fuel has been contaminated by other products or unauthorized additives. A standard for the density is that the fuel should be within the range of 775-840 kg/m$^3$ at 15° Celsius. The standard may reference external standards such as ASTM D1655. Standards for other equipment are known in the art or included in the annexed ATA 103 specification.

Figure 5G:
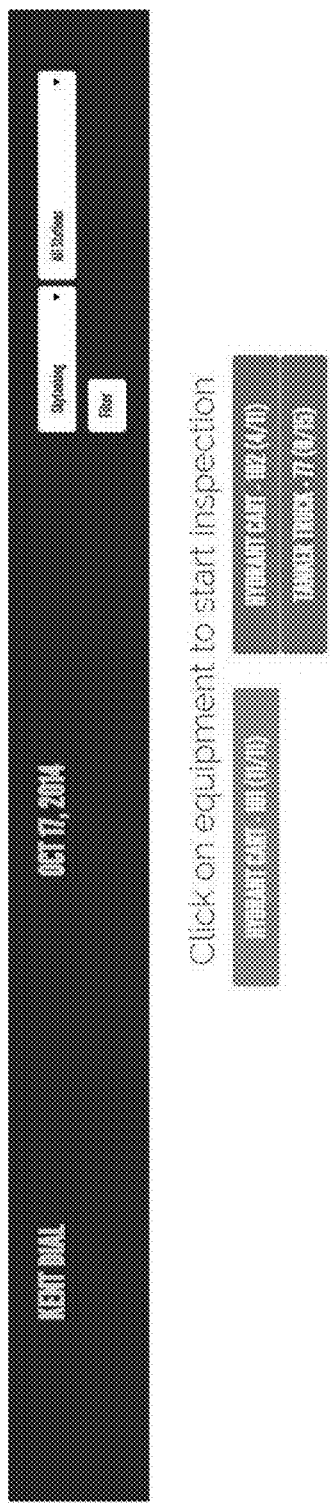
Figure 7C:
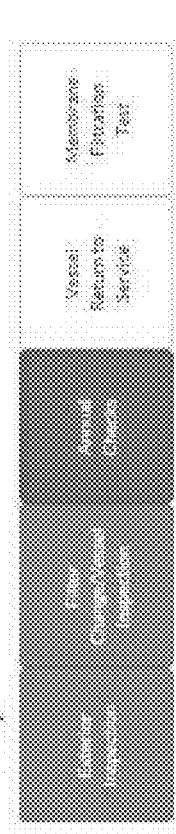
Figure 7C:
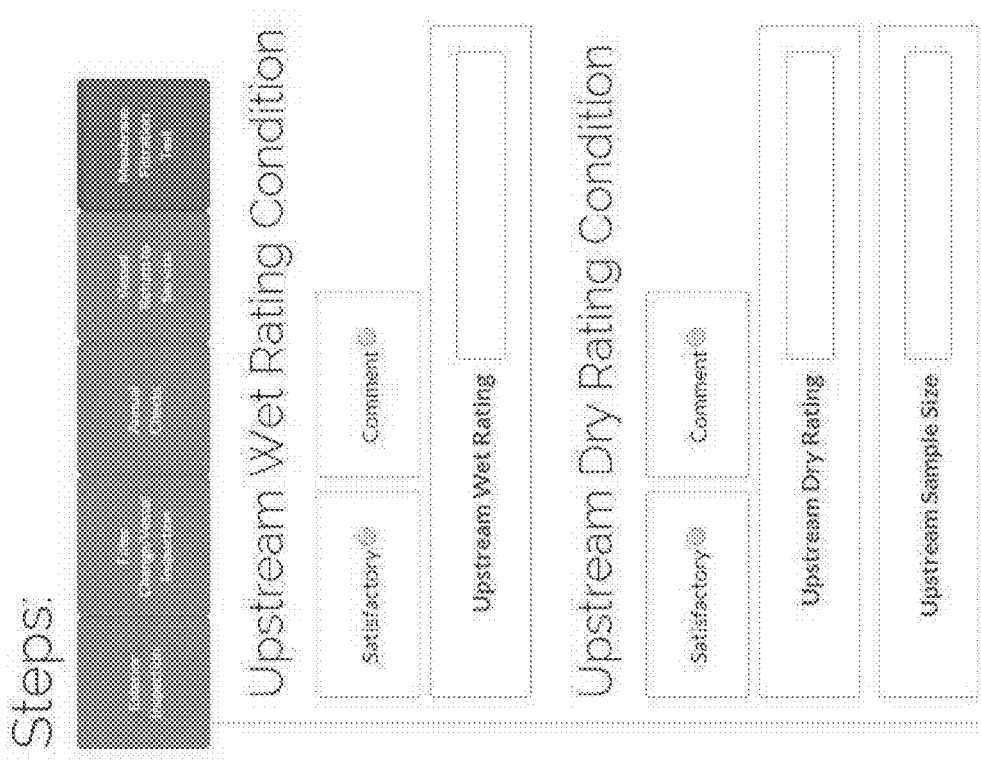
Figure 7G:
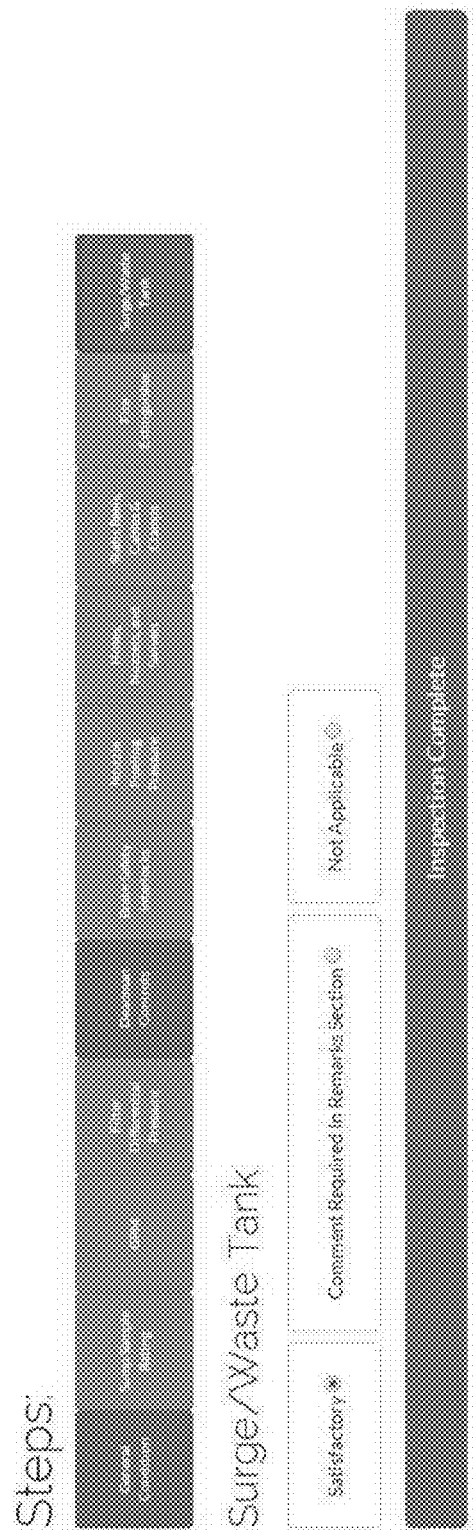

The inspection module 70 presents an interface for input on the portable computer 20 for completing and inputting the inspection 430. FIGS. 5g and 5h depict interfaces of initiating the inspection process with subject equipment. FIGS. 7a-7f illustrate a representative sequence of an inspection. Depicted are a series of interface states for an annual inspection for a filter vessel receiver 62. The inspection process was retrieved for a receiving vessel. The inspection module 70 interface presents a series of steps for the inspector to perform and standardized input for the inspection steps, where possible (FIGS. 7a-7e). The inspection module 70 interface presents a series of input elements for the inspection along with the resulting inspection condition, starting with the external condition and concluding with a membrane filtration inspection. FIG. 7f shows an input for camera input for documenting inspection conditions. The system stores the input, inspector, and the inspection date 440. The system processes the inspection report 440. For example, it may determine a pass or fail status if it is not directly input. FIG. 7g shows a completed inspection report from different jet fuel equipment.

In certain embodiments, the standardization of inspector input is accomplished by presentation of fixed input lists to the inspector for selection. Where free form text is desirable to document a condition, that approach is infeasible. In other embodiments, the inspection module 70 retrieves the prior free form text of the same input and prepopulates the input into the current inspection reports for the same jet fuel equipment 62. In exemplary configuration, the inspection module 70 retrieves a success or fail value of the prior inspection report for the same jet fuel equipment 62 and prepopulates the input value where a fail value exists in the prior inspect report, thus carrying forward the standardized description of the failure description. In this configuration, the prepopulated value is carried forward in inspection reports for the same equipment until a success value is received for the condition.

Further, upon a fail condition, appropriate parties may be notified for removal from service, repair, or remediation. For example, in a fuel inspection, if visible contamination of fuel is observed or found, aircraft refueling must be discontinued from that source. The system can notify all affected aircraft operators if it is anticipated that such contamination might impact operations and that fueling will not be resumed until the source of fuel contamination is found and removed. Fuel, suspected of possible contamination, will be held in quarantine until selected fuel quality, purity or specification tests have determined that it is acceptable for aircraft use.

Figure 8B:
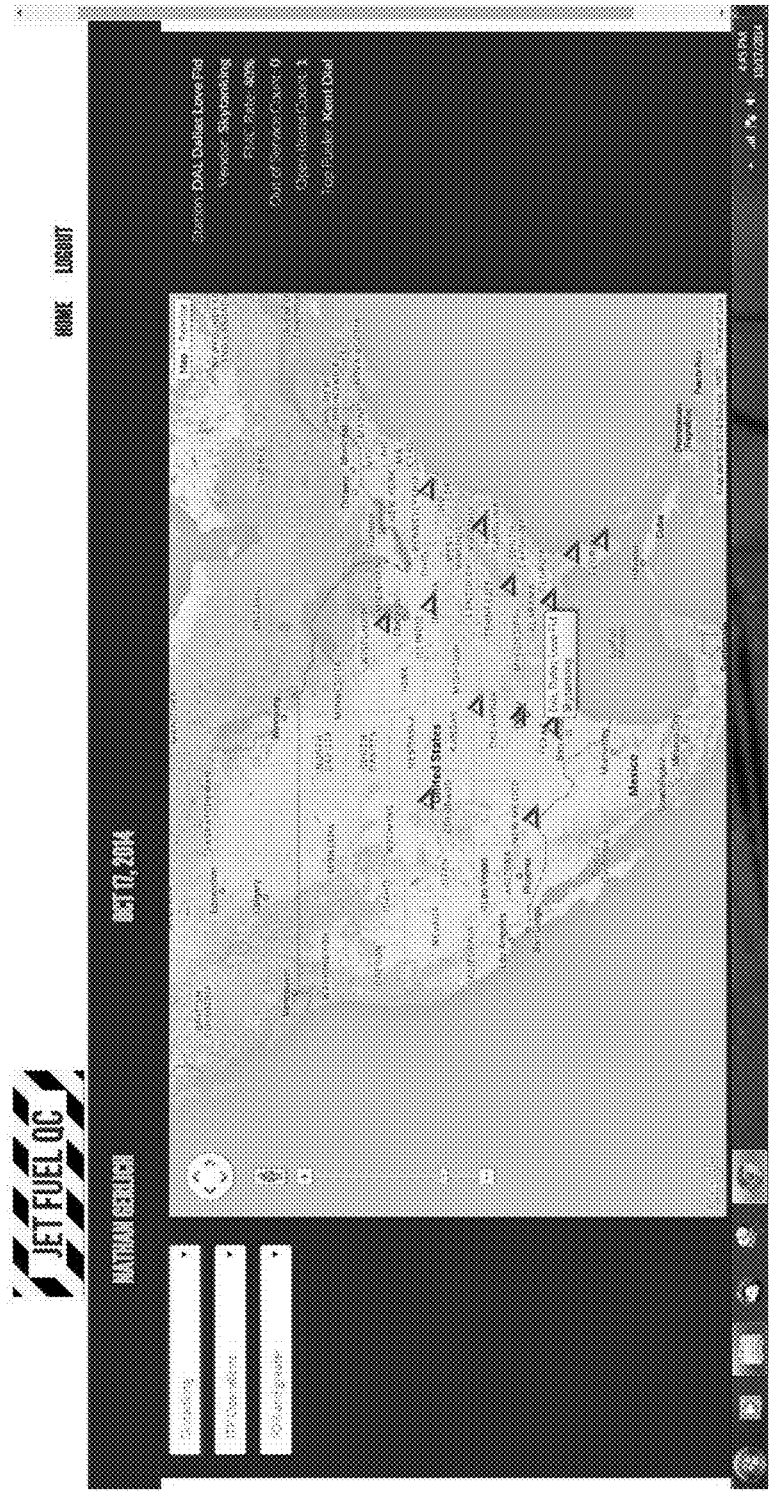
Figure 8C:

At step 500, inspection reports are generated. Jet fuel quality assurance, airport facility, and aircraft refueling equipment maintenance and training records are optimally readily available for inspection and review. Records should be signed, or be adequately identified by the person performing tasks or the person accepting responsibility that tasks were performed in accordance to the standards. The report module 50 generates reports showing average number of inspections for a given time period (FIG. 8a), inspection rates and results by location (FIG. 8b), pending inspections by inspector or facility with derived values such as the percentage of equipment in working order (FIG. 8c), or other reports based on equipment or inspections. In certain configurations, the jet fuel equipment 62 selected for reporting is based on absolute time. In other configurations, the jet fuel equipment 62 selected for reporting is based on time zone where it is deployed. For example, daily inspections may be determined using midnight of the time at which the jet fuel equipment is deployed. In processing for a larger report, the report module 50 polls the equipment in that time zone as the basis for the reporting deadline. The reports can be generated in real-time or near real-time.

Other reporting options include inspector scoring by different categories. In further configurations of the system, numeric values are assigned to completed inspections. In exemplary configuration, the assigned numeric values are weighted according to the safety risk, past compliance at an individual or group level, target compliance areas, or other factors. FIG. 9 shows a report of completed inspections with assigned values for an inspector.

Figure 10A:
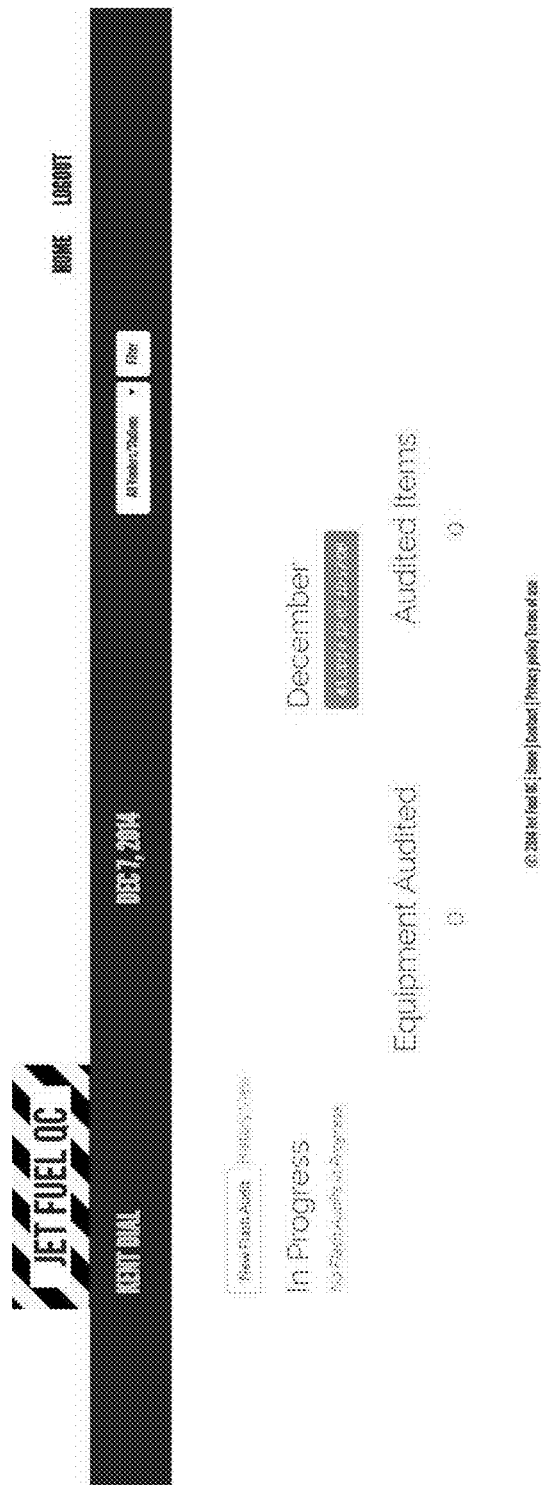
FIGS. 10a-10o depict representative screens for the spot audit process.
Figure 10B:
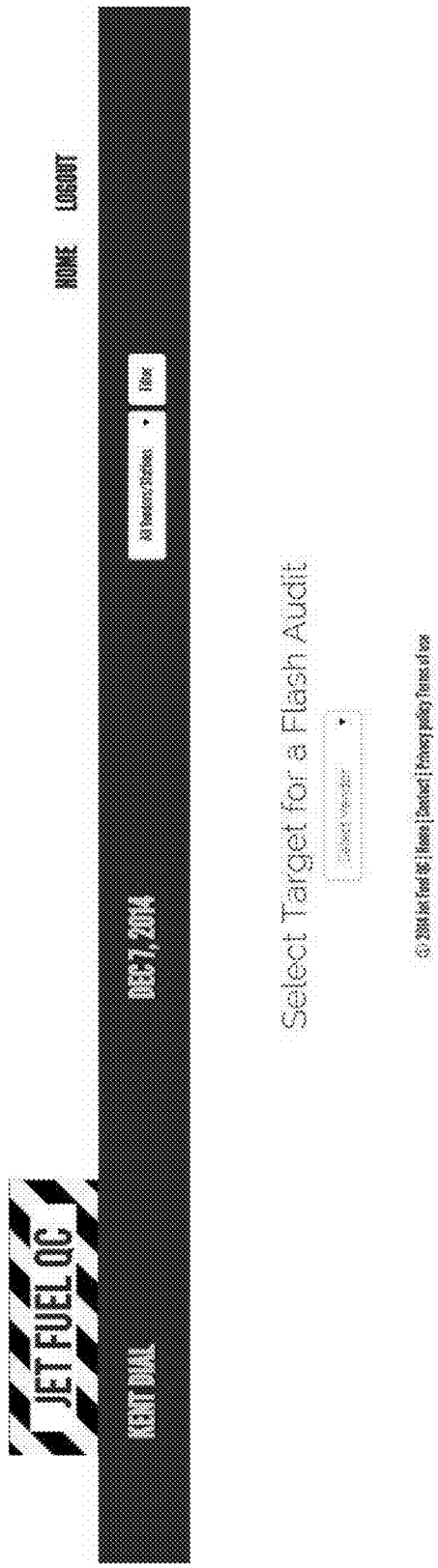
Figure 10C:
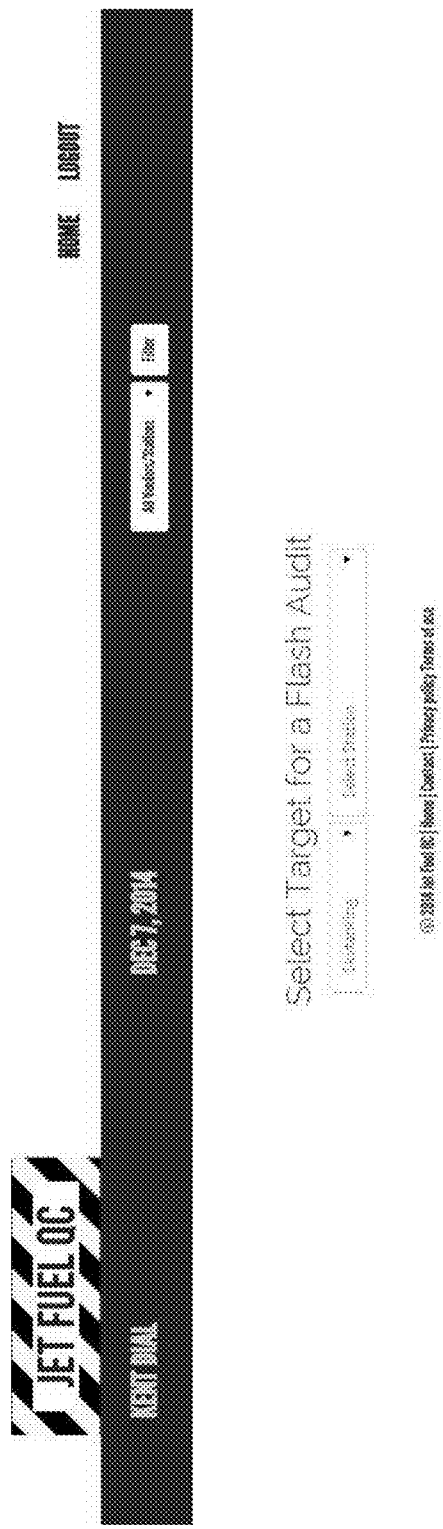
Figure 10D:
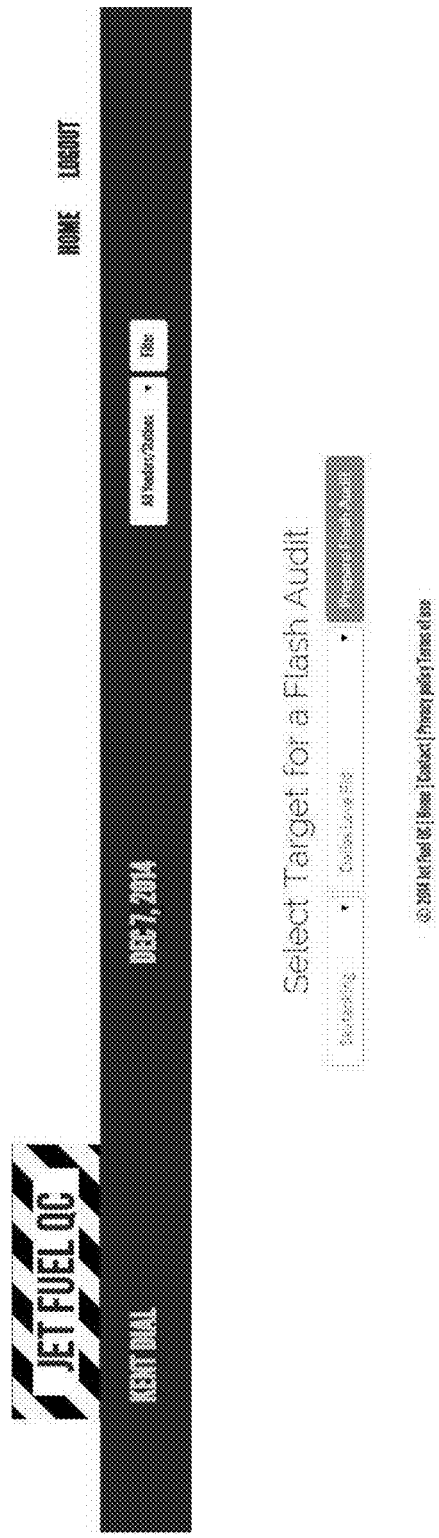
Figure 10E:
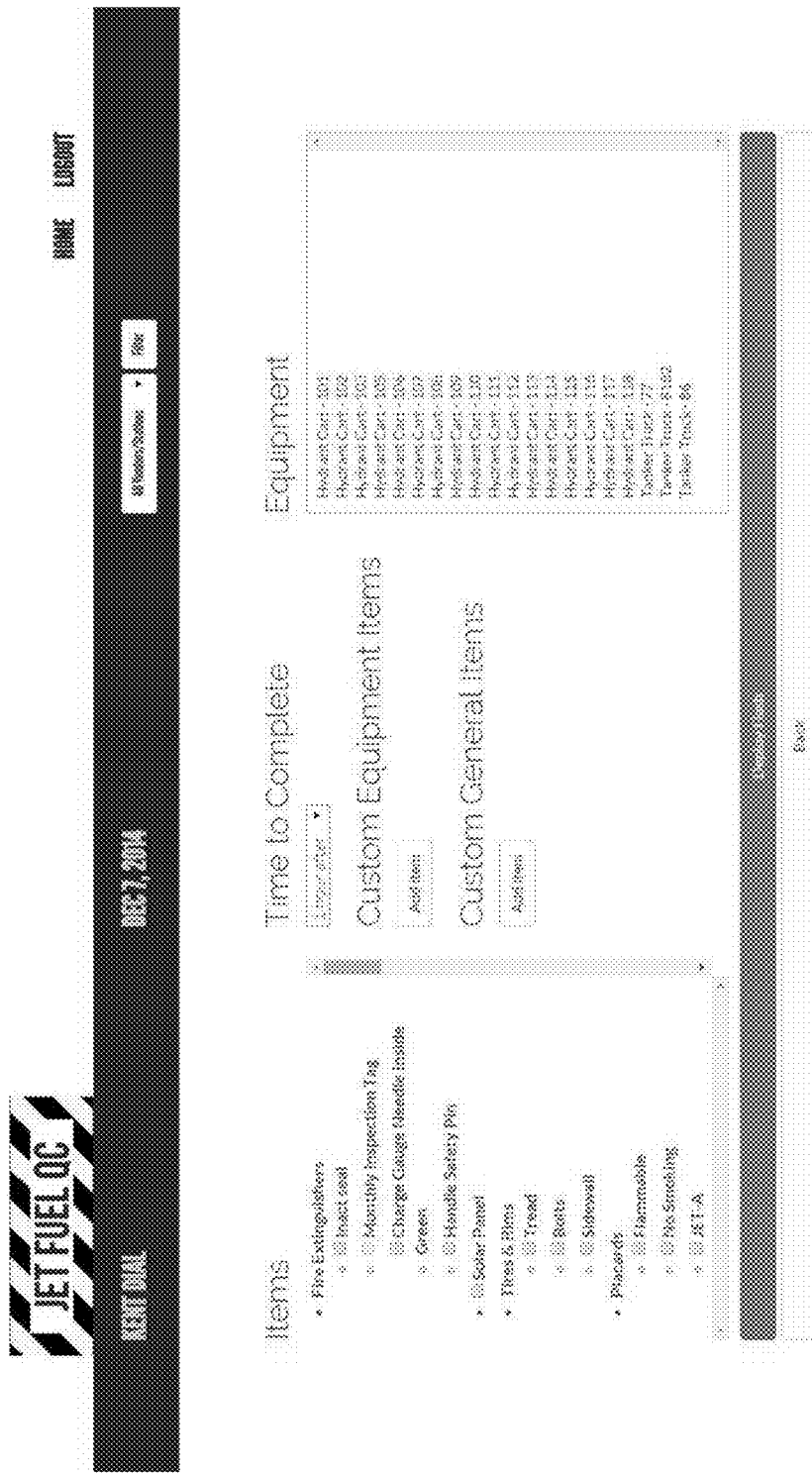
Figure 10F:
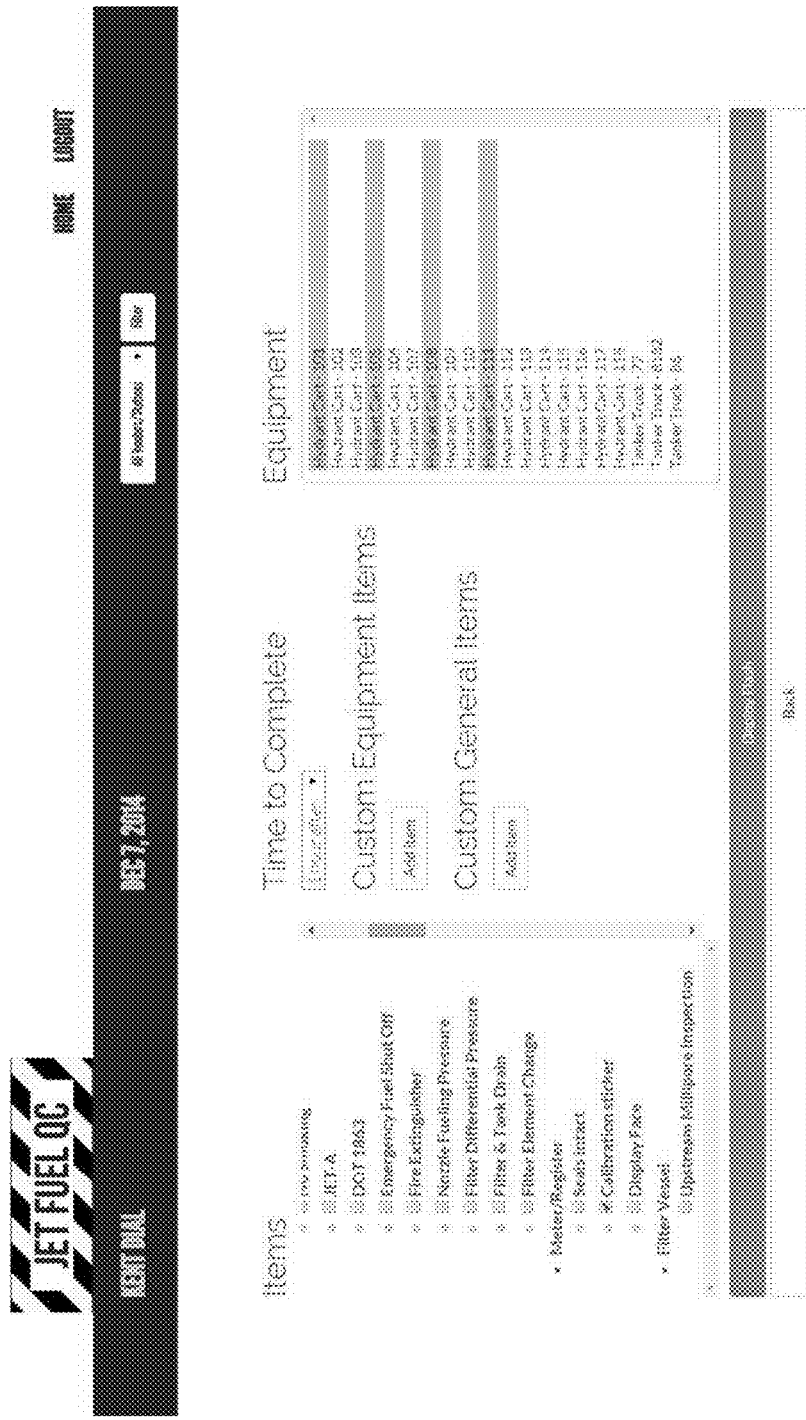
Figure 10G:
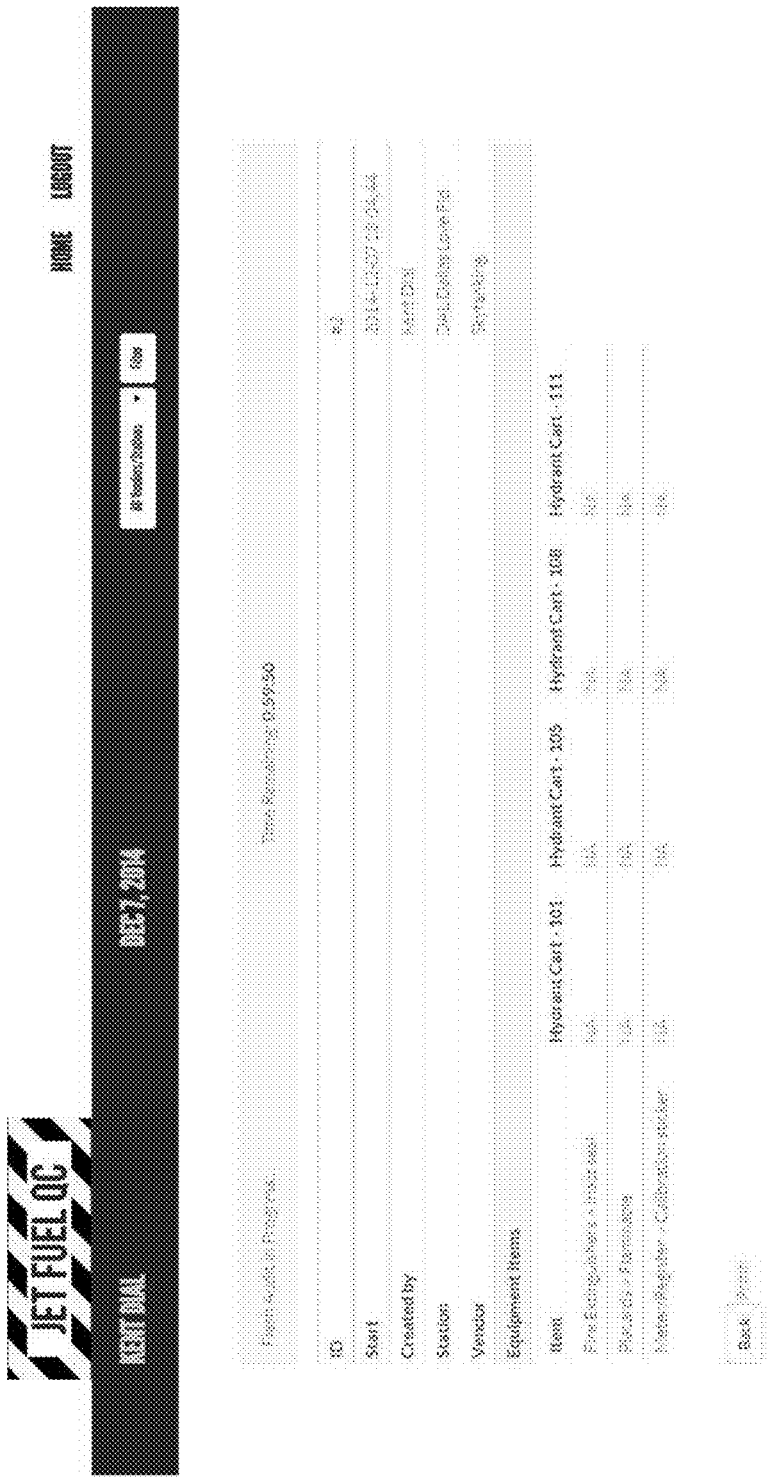
Figure 10H:
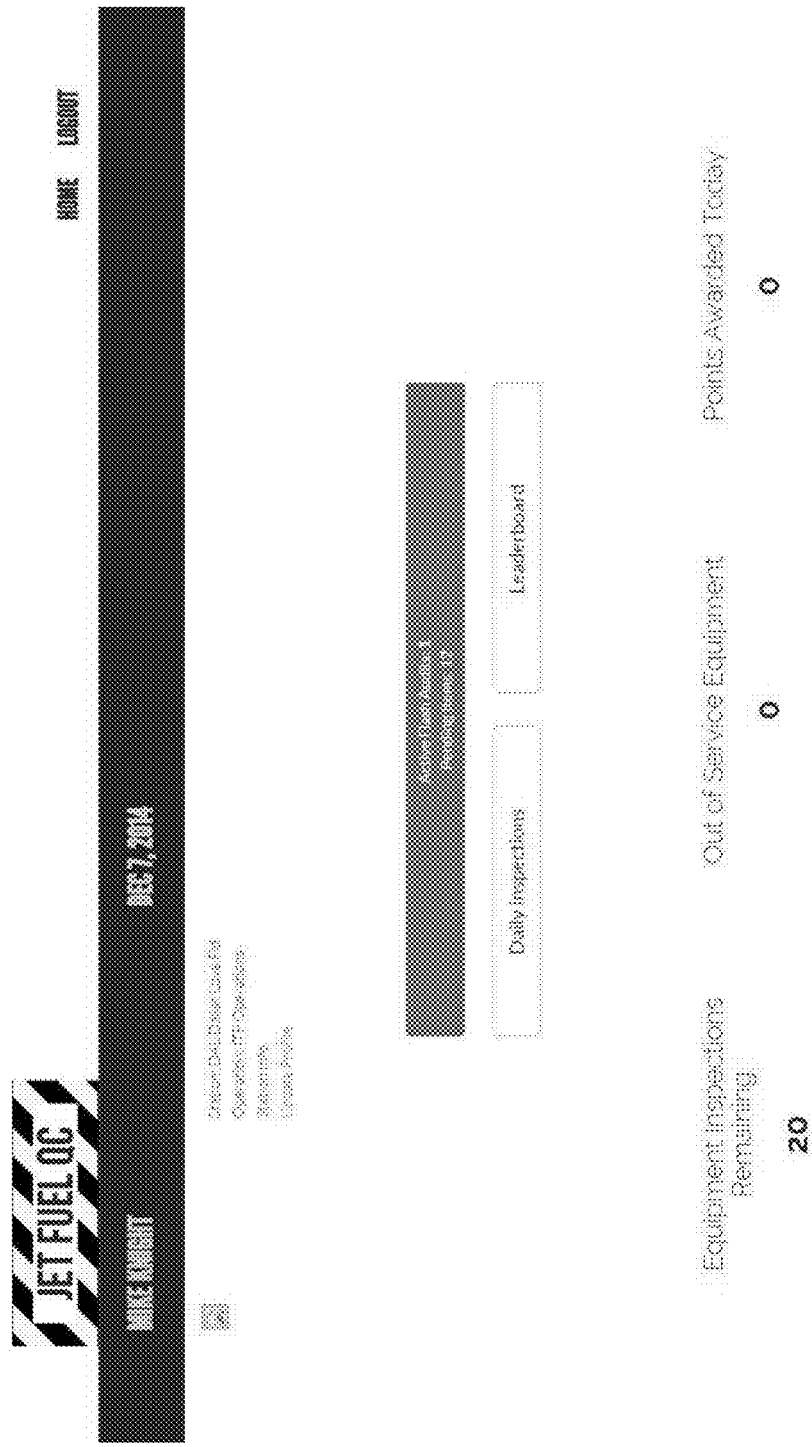
Figure 101:
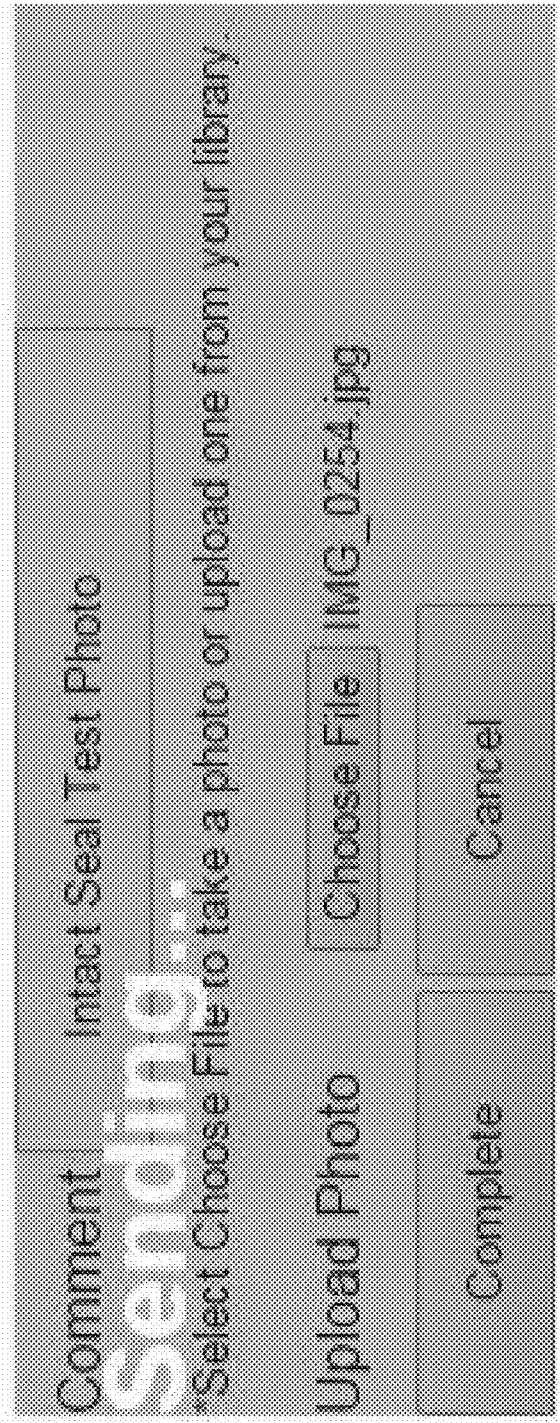
Figure 10M:
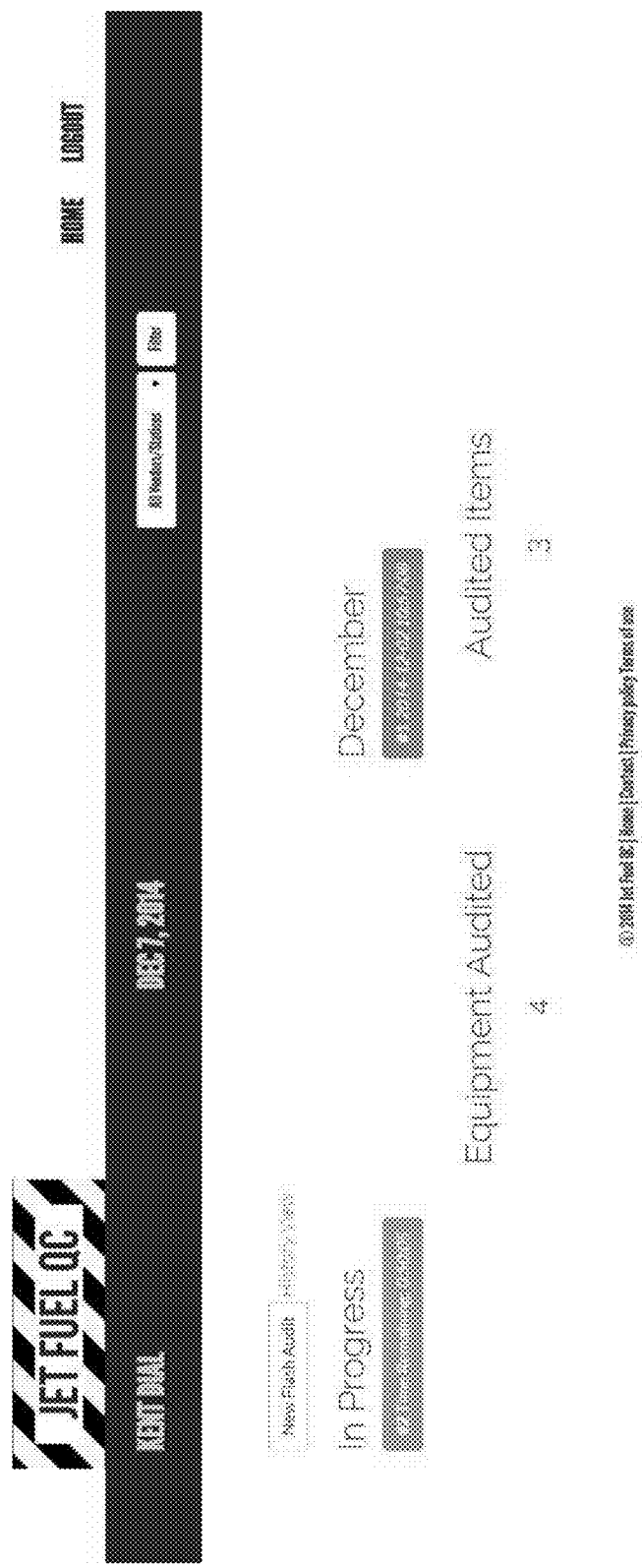
Figure 10N:
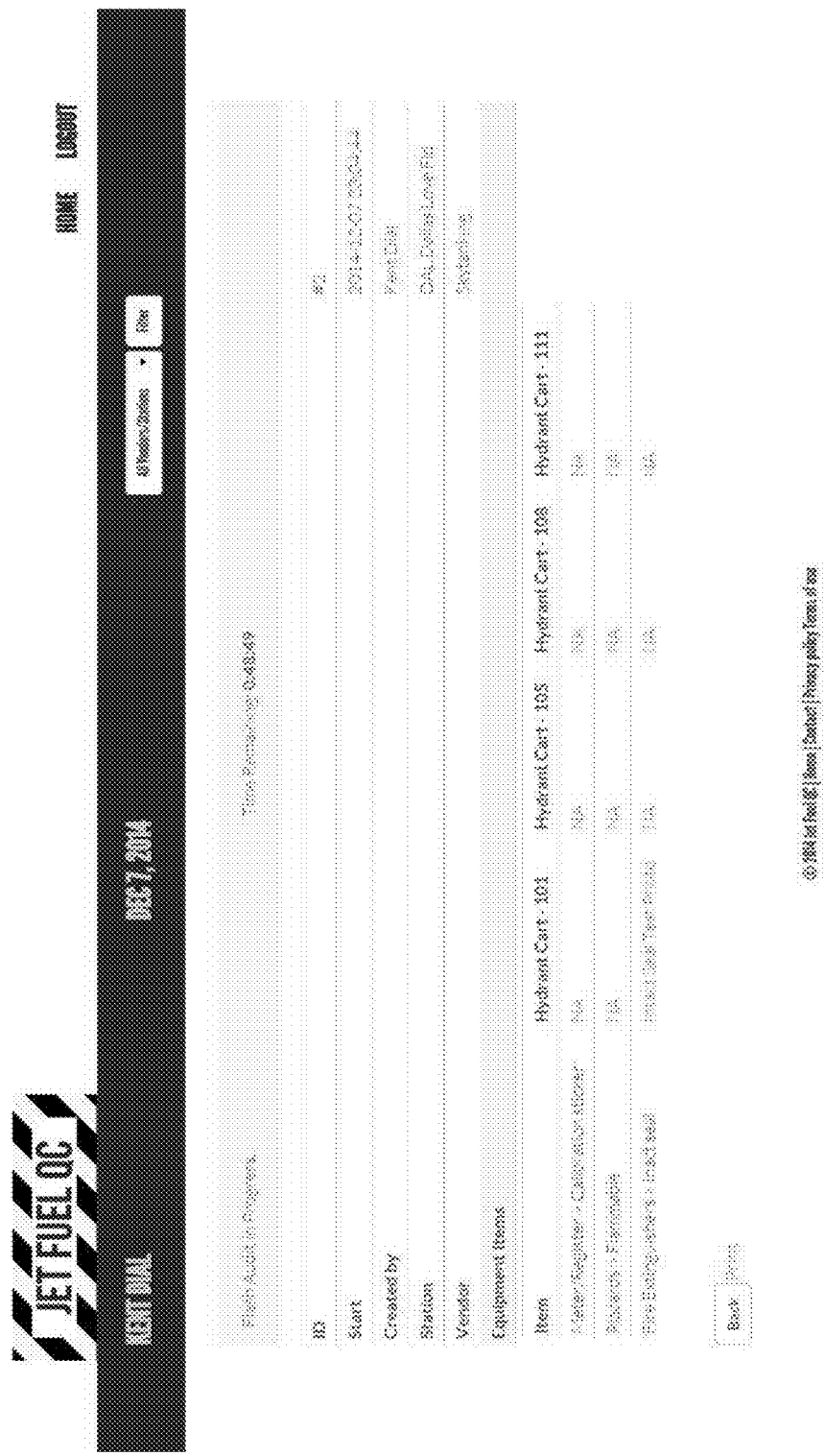
Figure 10O:
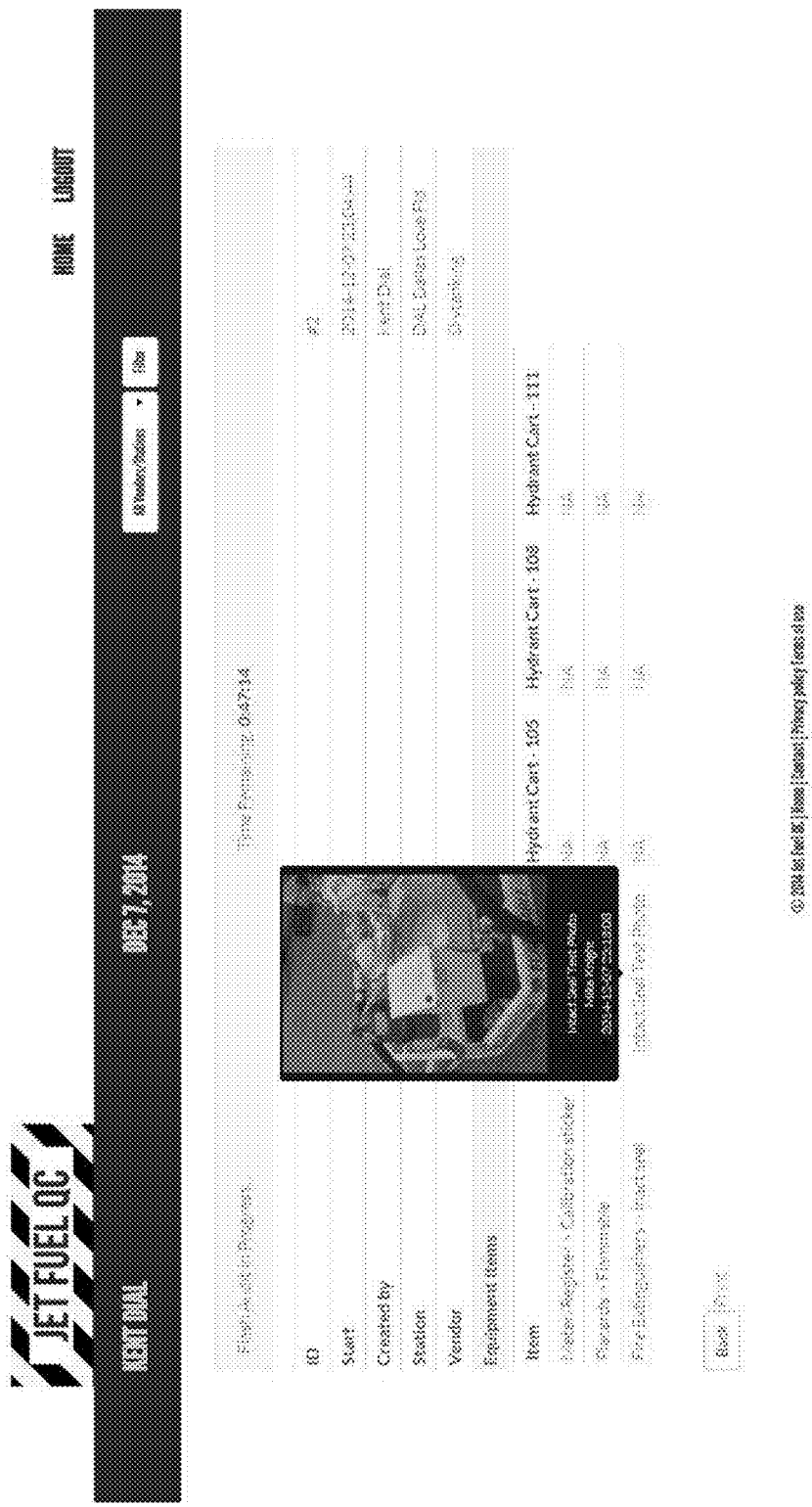

FIGS. 10a-10o show representative screens of a "spot audit" process, one that permits an auditor, such as a third party government authority, to remotely initiate and monitor an inspection in near real-time. To initiate a spot audit, the auditor selects a target location being monitored by the system. FIG. 10b-d show a site being selected for inspection. After selecting the location, all of the jet fuel equipment 62 monitored in that location is retrieved for selection input into a list in an interface of all available auditable items. The auditor selects items from this list, and then inputs an amount of time to allow completion of the spot audit. FIGS. 10e-g show the spot audit parameters, such as the time and the equipment, being input.

The system then sends alerts to all inspectors in that location that a spot audit has been activated. Inspectors at that location receive the list of jet fuel equipment 62 to audit. In order to complete an audit item, the user completes an inspection, submits a picture of the item, and optionally adds a comment, and then upload them to via the spot audit interface. FIGS. 10*h-l* show the inspector inputting the status of the selected equipment and optionally inputting photo evidence. The audit items are viewable in real-time by the auditor as they are accomplished. The spot audit concludes when either all the items have been completed or the allowance of time has passed. A list is maintained in the spot audit interface of all audits in the calendar month for each location. Audit details and results are stored in the equipment database 40 and may be designated with by insignia, color codes, or other means in the art. FIGS. 10*m-o* show monitoring the status and completion of the spot audit.

Insofar as the description above and the accompanying drawing disclose any additional subject matter that is not within the scope of the single claim below, the inventions are not dedicated to the public and the right to file one or more applications to claim such additional inventions is reserved.

What is claimed is:

1. A system for monitoring jet fuel quality control procedural compliance, said system comprising:
   an equipment module having an equipment database and causing a processor and memory to carry out instructions;
   an equipment database operable to store jet fuel equipment data and jet fuel equipment inspection reports;
   the equipment module storing said inspection reports processes, each inspection report customized to a particular type of jet fuel equipment;
   said inspection reports including inspection steps, one or more tests, and input to document said test, and a test result;
   the system presenting an interactive interface for receiving input, storage, and processing of jet fuel and jet fuel equipment said inspections reports;
   wherein said jet fuel equipment data includes a facility location and a time zone.

2. A system for monitoring jet fuel quality control procedural compliance, said system comprising:
   an equipment module having an equipment database and causing a processor and memory to carry out instructions;
   an equipment database operable to store jet fuel equipment data and jet fuel equipment inspection reports;
   the equipment module storing said inspection reports processes, each inspection report customized to a particular type of jet fuel equipment;
   said inspection reports including inspection steps, one or more tests, and input to document said test, and a test result;
   the system presenting an interactive interface for receiving input, storage, and processing of jet fuel and jet fuel equipment said inspections reports;
   further comprising a spot audit module, said spot audit module receiving a remote inspection request for selected jet fuel equipment at a location, sending an alert to inspectors at said location to initiate an inspection of said jet fuel equipment, receiving an inspection report input from said inspector and transmitting said inspection report input to said auditor in real-time.

3. A process for monitoring jet fuel quality control procedural compliance, said process comprising:
   providing an equipment module having an equipment database and causing a processor and memory to carry out instructions;
   an equipment database operable to store jet fuel equipment data and jet fuel equipment inspection reports;
   the equipment module storing said inspection reports processes, each inspection report customized to a particular type of jet fuel equipment;
   said inspection reports including inspection steps, one or more tests, and input to document said test, and a test result;
   the system presenting an interactive interface for receiving input, storage, and processing of jet fuel and jet fuel equipment said inspection reports;
   wherein said jet fuel equipment data includes a facility location and a time zone.

4. A process for monitoring jet fuel quality control procedural compliance, said process comprising:
   providing an equipment module having an equipment database and causing a processor and memory to carry out instructions;
   an equipment database operable to store jet fuel equipment data and jet fuel equipment inspection reports;
   the equipment module storing said inspection reports processes, each inspection report customized to a particular type of jet fuel equipment;
   said inspection reports including inspection steps, one or more tests, and input to document said test, and a test result;
   the system presenting an interactive interface for receiving input, storage, and processing of jet fuel and jet fuel equipment said inspections reports;
   further comprising a spot audit module, said spot audit module receiving a remote inspection request for selected jet fuel equipment at a location, sending an alert to inspectors at said location to initiate an inspection of said jet fuel equipment, receiving an inspection report input from said inspector and transmitting said inspection report input to said auditor in real-time.

5. The system of claim 2, wherein said inspection input includes camera input.

6. The process of claim 4, wherein said spot audit module receives an amount of time for completion of the spot audit by the inspector and monitors whether said inspection report is completed within said amount of time.

* * * * *